US007956196B2

(12) United States Patent
Bonfanti et al.

(10) Patent No.: US 7,956,196 B2
(45) Date of Patent: Jun. 7, 2011

(54) 1,3-DIHYDRO-BENZIMIDAZOL-2-YLIDENE AMINES AS INHIBITORS OF RESPIRATORY SYNCYTIAL VIRUS REPLICATION

(75) Inventors: Jean-François Bonfanti, Ande (FR); Jérôme Michel Claude Fortin, Igoville (FR); Ismet Dorange, Ande (FR)

(73) Assignee: Tibotec Pharmaceuticals Ltd. (IE)

( * ) Notice: Subject to any disclaimer, the term of this patent is extended or adjusted under 35 U.S.C. 154(b) by 776 days.

(21) Appl. No.: 11/908,538

(22) PCT Filed: Mar. 17, 2006

(86) PCT No.: PCT/EP2006/060852

§ 371 (c)(1),
(2), (4) Date: Sep. 13, 2007

(87) PCT Pub. No.: WO2006/097534

PCT Pub. Date: Sep. 21, 2006

(65) Prior Publication Data

US 2008/0146564 A1 Jun. 19, 2008

(30) Foreign Application Priority Data

Mar. 17, 2005 (EP) .................................... 05102127

(51) Int. Cl.

| | |
|---|---|
| *A61K 31/4184* | (2006.01) |
| *A61K 31/5377* | (2006.01) |
| *C07D 235/30* | (2006.01) |
| *C07D 401/12* | (2006.01) |
| *C07D 401/14* | (2006.01) |
| *C07D 413/14* | (2006.01) |

(52) U.S. Cl. ..................... 548/307.4; 544/128; 544/139; 546/181; 546/273.4; 514/234.5; 514/338; 514/318; 514/314; 514/388

(58) Field of Classification Search ................ 548/307.4
See application file for complete search history.

(56) References Cited

FOREIGN PATENT DOCUMENTS

| | | |
|---|---|---|
| DE | 2003825 | 12/1970 |
| WO | WO 01/00611 | 1/2001 |
| WO | WO 01/00612 | 1/2001 |
| WO | WO 01/00615 | 1/2001 |

OTHER PUBLICATIONS

Zvezdina et al., Khimiya Geterotsiklicheskikh Soedinenii (1970), (3), pp. 419-421.*
Zvezdina et al., CA 73:25362, 1970.*
An English translation of Zvezdina et al., Khimiya Geterotsiklicheskikh Soedinenii (1970), (3), pp. 419-421.*
An English translation of Anisimova et al., Khimiya Geterotsiklicheskikh Soedinenii (1976), (1), pp. 121-125.*
Chemical Abstracts Registry No. 784992-40-1, indexed in the Registry file on STN Nov. 19, 2004.*
Schickli et al., Human Vaccines, vol. 5, Issue 9, pp. 582-591, Sep. 2009.*
International Search Report—PCT/EP2006/060852; May 23, 2006—TIP-0070USPCT.

* cited by examiner

*Primary Examiner* — Laura L. Stockton

(57) ABSTRACT

Novel 1,3-dihydro-benzimidazol-2-ylidene amine derivatives of formula (I)

the addition salts and stereochemically isomeric forms wherein each Alk is $C_{1-6}$alkanediyl; Q is hydrogen; $C_{1-6}$alkyl substituted with one or two $Ar^2$ radicals; $C_{1-6}$alkyl substituted with quinolinyl, oxazolidinyl, thiazolidinyl, morpholinyl, thiomorpholinyl, or with pyrrolidinonyl; —CO—$Ar^2$; or Q is a radical of formula wherein t is 1, 2 or 3; $R^4$ is amino, mono-or di($C_{1-6}$alkyl) amino;
$R^1$ is $Ar^2$, —CO—$Ar^2$ or a monocyclic or bicyclic heterocycle which may optionally be substituted; $R^2$ is as $R^1$ and additionally can be hydrogen; where Q is other than hydrogen, $R^3$ is hydrogen; and where Q is other than hydrogen, $R^3$ is a radical:

(b)

wherein $R^6$ is hydrogen, $C_{1-6}$alkyl, substituted $C_{1-6}$alkyl; $R^7$, $R^8$, $R^9$ are halo, cyano, $C_{1-6}$alkyl, substituted $C_{1-6}$alkyl, $C_{2-6}$alkenyl, cyano$C_{2-6}$alkenyl, $C_{2-6}$alkynyl, cyano$C_{2-6}$alkynyl, $Ar^1$, $R^{10a}$—0—, $R^{10a}$—S—, —N($R^{5a}R^{5b}$), $R^{10a}$—O—C(═O)—, N($R^{5a}R^{5b}$)—C(═O)—, $R^{10a}$—C(═O)—$NR^{5b}$—, $R^{10b}$—C(═O)—O—; and $R^8$ and/or $R^9$ may also be hydrogen; which are RSV inhibitors. Compositions containing these compounds and processes for preparing these compounds and compositions.

19 Claims, No Drawings

1,3-DIHYDRO-BENZIMIDAZOL-2-YLIDENE AMINES AS INHIBITORS OF RESPIRATORY SYNCYTIAL VIRUS REPLICATION

This application is a National Stage application under 35 U.S.C. 371 of PCT International Application No. PCT/EP2006/060852, filed Mar. 17, 2006, which claims priority from European Patent Application No. EP 05102127.7, filed Mar. 17, 2005.

The present invention concerns 1,3-dihydro-benzimidazol-2-ylidene amine derivatives having inhibitory activity on the replication of the respiratory syncytial virus (RSV), the preparation thereof and pharmaceutical compositions comprising these compounds as active ingredient.

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, RespiGam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drugs against RSV replication.

WO-01/00615, WO-01/00611 and WO-01/00612 describe a series of benzimidazole derivatives having RSV inhibitory properties. The present invention is aimed at providing further RSV inhibitory compounds which are 1,3-dihydro-benzimidazol-2-ylidene amine derivatives, structurally unrelated to these prior art compounds.

The present invention concerns inhibitors of RSV replication, which can be represented by formula (I)

the addition salts thereof; and the stereochemically isomeric forms thereof; wherein each Alk independently is $C_{1-6}$alkanediyl;

Q is hydrogen; $C_{1-6}$alkyl substituted with one or two $Ar^2$ radicals; $C_{1-6}$alkyl substituted with quinolinyl, oxazolidinyl, thiazolidinyl, morpholinyl, thiomorpholinyl, or with pyrrolidinonyl; —CO—$Ar^2$; or Q is a radical of formula (a)

wherein t is 1, 2 or 3;

$R^4$ is amino, mono- or di($C_{1-6}$alkyl)amino;

$R^1$ is $Ar^2$, —CO—$Ar^2$ or a monocyclic or bicyclic heterocycle selected from piperidinyl, piperazinyl, morpholinyl, thiomorpholinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]pyridinyl and 2,3-dihydro-1,4-dioxino[2,3-b]pyridyl;

wherein each of said monocyclic or bicyclic heterocycles may optionally be substituted with 1, 2, or 3 substituents each independently selected from the group consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-oxycarbonyl and —C(=O)—$NR^{5a}R^{5b}$;

$R^2$ independently has the same meanings of $R^1$ and additionally can be hydrogen;

where Q is other than hydrogen, $R^3$ is hydrogen; or where Q is hydrogen, $R^3$ is a radical of formula:

(b)

wherein $R^6$ is selected from hydrogen, $C_{1-6}$alkyl, $Ar^2C_{1-6}$alkyl, hydroxy$C_{1-6}$alkyl, ($C_{1-6}$alkyloxy)-$C_{1-6}$alkyl, amino$C_{1-6}$ alkyl, mono- and di($C_{1-6}$alkyl)amino-$C_{1-6}$alkyl, carboxyl$C_{1-6}$alkyl, $C_{1-6}$alkyloxycarbonyl$C_{1-6}$alkyl, aminocarbonyl$C_{1-6}$alkyl, mono- and di($C_{1-6}$alkyl)aminocarbonyl$C_{1-6}$alkyl;

$R^7$, $R^8$, $R^9$ each independently are selected from halo, cyano, $C_{1-6}$alkyl, $Ar^1$—$C_{1-6}$alkyl, cyano$C_{1-6}$alkyl, $C_{2-6}$alkenyl, cyano$C_{2-6}$alkenyl, $C_{2-6}$alkynyl, cyano$C_{2-6}$alkynyl, $Ar^1$, $R^{10a}$—O—, $R^{10a}$—S—, —$N(R^{5a}R^{5b})$, polyhalo$C_{1-6}$alkyl, $R^{10a}$—O—C(=O)—, $N(R^{5a}R^{5b})$—C(=O)—, $R^{10a}$—O—$C_{1-6}$alkyl, $N(R^{5a}R^{5b})$—$C_{1-6}$alkyl, $R^{10a}$—O—C(=O)—$C_{1-6}$alkyl, $N(R^{5a}R^{5b})$—C(=O)—$C_{1-6}$alkyl, $R^{10a}$—C(=O)—$NR^{5b}$, $R^{10b}$—C(=O)—O—, $R^{10b}$—C(=O)—O—$C_{1-6}$alkyl; and $R^8$ and/or $R^9$ may also be hydrogen;

each $R^{5a}$ and $R^{5b}$ independently from each other are hydrogen or $C_{1-6}$alkyl;

$R^{10a}$ is hydrogen, $C_{1-6}$alkyl or $Ar^1C_{1-6}$alkyl;

$R^{10b}$ is $C_{1-6}$alkyl or $Ar^1C_{1-6}$alkyl;

$Ar^1$ is phenyl or phenyl substituted with 1, 2, 3 or 4 substituents independently selected from halo, hydroxy, $C_{1-6}$alkyl, hydroxy$C_{1-6}$alkyl, polyhalo$C_{1-6}$alkyl and $C_{1-6}$alkyloxy;

$Ar^2$ is phenyl or phenyl substituted with 1, 2, 3 or 4 substituents independently selected from halo, hydroxy, $C_{1-6}$alkyl, cyano, nitro, hydroxy$C_{1-6}$alkyl, polyhalo$C_{1-6}$alkyl, $C_{1-6}$alkyloxy, hydroxy$C_{1-6}$alkyloxy, $C_{1-6}$alkyloxycarbonyl, $Ar^1$ and $Ar^1O$.

As used hereinbefore or hereinafter "$C_{1-4}$alkyl" as a group or part of a group defines straight or branched chain saturated hydrocarbon radicals having from 1 to 4 carbon atoms such as methyl, ethyl, 1-propyl, 2-propyl, 1-butyl, 2-butyl, 2-methylpropyl, t.butyl; "$C_{1-6}$alkyl" as a group or part of a group defines straight or branched chain saturated hydrocarbon radicals having from 1 to 6 carbon atoms such as the group defined for $C_{1-4}$alkyl and 1-pentyl, 2-pentyl, 1-hexyl, 2-hexyl, 3-hexyl, 2-methylbutyl, 3-methylpentyl and the like; "$C_{1-2}$alkyl" defines methyl or ethyl. Preferred amongst $C_{1-6}$alkyl are $C_{1-4}$alkyl and $C_{1-2}$alkyl.

The term "$C_{3-6}$alkenyl" used herein as a group or part of a group is meant to comprise straight or branched chain unsaturated hydrocarbon radicals having at least one double bond, and preferably having one double bond, and from 3 to 6 carbon atoms such as 1-propenyl, 2-propenyl (or allyl), 1-butenyl, 2-butenyl, 3-butenyl, 2-methyl-2-propenyl, 1-pentenyl, 2-pentenyl, 3-pentenyl, 2-methyl-1-butenyl, 1-hexenyl, 2-hexenyl, 3-hexenyl, 4-hexenyl, 2-methyl-2-pentenyl, 1,2-dimethyl-1-butenyl and the like. The term "$C_{2-6}$alkenyl" used herein as a group or part of a group is meant to comprise $C_{3-6}$alkenyl groups and ethylene(or vinyl). The term "$C_{3-6}$alkynyl" defines straight or branched chain unsaturated hydrocarbon radicals having one triple bond and from 3 to 6 carbon atoms such as propenyl, butyn-1-yl, butyn-2-yl, pentyn-1-yl, pentyn-2-yl, hexyn-1-yl, hexyn-2-yl, hexyn-3-yl, 2-methylbutyn-1-yl, and the like. The term "$C_{2-6}$alkynyl" used herein as a group or part of a group is meant to comprise —$C_{3-6}$alkynyl groups and ethynyl.

$C_{1-4}$alkanediyl defines bivalent straight and branched chain saturated hydrocarbon radicals having from 1 to 4 carbon atoms such as, for example, methylene, 1,2-ethanediyl (ethylene), 1,3-propanediyl, 1,4-butanediyl, 1,2-propanediyl, 2,3-butanediyl, 1,5-pentanediyl and the like $C_{1-6}$alkanediyl is meant to include $C_{1-4}$alkanediyl and the higher homologues thereof having from 5 to 6 carbon atoms such as, for example, 1,5-pentanediyl, 1,6-hexanediyl and the like. Preferred amongst $C_{1-6}$alkanediyl are $C_{1-4}$alkanediyl.

As used herein before, the term (=O) forms a carbonyl moiety when attached to a carbon atom, a sulfoxide moiety when attached to a sulfur atom and a sulfonyl moiety when two of said terms are attached to a sulfur atom.

The terms carboxyl, carboxy or hydroxycarbonyl refer to a group —COOH.

The term halo is generic to fluoro, chloro, bromo and iodo.

As used in the foregoing and hereinafter, "polyhalo$C_{1-6}$alkyl" as a group or part of a group, e.g. in polyhalo$C_{1-6}$alkyloxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Also included are perfluoro $C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo-$C_{1-4}$alkyl, the halogen atoms may be the same or different.

A hydroxy$C_{1-6}$alkyl or an amino$C_{1-6}$alkyl group when substituted on an oxygen atom or a nitrogen atom preferably is a hydroxy$C_{2-6}$alkyl group wherein the hydroxy group and the oxygen or nitrogen is separated by at least two carbon atoms or a amino$C_{2-6}$alkyl group wherein the amino group and the nitrogen atom is separated by at least two carbon atoms. Preferred among the ($C_{1-6}$alkyloxy)$C_{1-6}$alkyl or mono- or di($C_{1-6}$alkyl)amino-$C_{1-6}$alkyl groups, when substituted on a nitrogen atom are the ($C_{1-6}$alkyloxy)$C_{2-6}$alkyl or mono- or di($C_{1-6}$alkyl)amino-$C_{2-6}$alkyl groups wherein the $C_{1-6}$alkyloxy group and the nitrogen atom and the mono- or di($C_{1-6}$alkyl)amino group and the nitrogen atom are separated by at least two carbon atoms.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any moiety, each definition is independent.

Whenever used hereinafter, the term "compounds of formula (I)", or "the present compounds" or similar term is meant to include the compounds of formula (I), the addition salts and stereochemically isomeric forms.

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphor sulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), and the intermediates used in the preparation thereof, the absolute stereochemical configuration may not have been experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counter ion is pharmaceutically acceptable. However, salts of acids and bases, which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "compounds of formula (I)", or any similar terms such as "compounds of the invention" and the like, is meant to also comprise any prodrugs that the compounds of formula (I) may form. The term "prodrug" as used herein is meant to comprise any pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, $8^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-7}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring. Alkanoyl esters for example are any $C_{1-30}$alkanoyl esters, in particular $C_8$-30alkanoyl esters, more in particular $C_{10-24}$alkanoyl esters, further in particular $C_{16}$-20alkanoyl esters, wherein the alkyl part may have one or more double bonds. Examples of alkanoyl esters are decanoate, palmitate and stearate.

The term "compounds of formula (I)", or any similar terms such as "compounds of the invention" and the like, is meant to also comprise any metabolites that are formed in vivo upon administration of the drug. Some examples of metabolites in accordance with the invention include, but are not limited to, (a) where the compound of formula (I) contains a methyl group, a hydroxymethyl derivative thereof; (b) where the compound of formula (I) contains an alkoxy group, an hydroxy derivative thereof; (c) where the compound of formula (I) contains a tertiary amino group, a secondary amino derivative thereof; (d) where the compound of formula (I) contains a secondary amino group, a primary derivative thereof; (e) where the compound of formula (I) contains a phenyl moiety, a phenol derivative thereof; and (f) where the compound of formula (I) contains an amide group, a carboxylic acid derivative thereof.

The term "compounds of formula (I)", or any similar terms such as "compounds of the invention" and the like, is meant to also comprise any N-oxide forms of the compounds of formula (I), which are compounds of formula (I) wherein one or several nitrogen atoms are oxidized to the N-oxide form.

The compounds of formula (I) may have metal binding, chelating and/or complex forming properties and therefore may exist as metal complexes or metal chelates. Such metal complex derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

A number of subgroups of compounds of formula (I) are specified hereafter by restricted definitions of the various radicals in the compounds of formula (I). These subgroups however are also meant to comprise those with any permutation of the restricted definitions mentioned hereinafter.

Subgroups I of the compounds of formula (I) are those compounds of formula (I), or any subgroup of compounds of formula (I) specified herein, wherein
(a) one or more of the radicals Alk is $C_{1-4}$alkanediyl;
(b) wherein one or more of the radicals Alk is $C_{1-2}$alkanediyl;
(c) wherein one or more of the radicals Alk is methylene; or
(d) wherein all of the radicals Alk are methylene.

Subgroups II of the compounds of formula (I) are those compounds of formula (I), or any subgroup of compounds of formula (I) specified herein, such as the subgroups I mentioned above, wherein
(a) Q is $C_{1-6}$alkyl substituted with one or two $Ar^2$ radicals; $C_{1-6}$alkyl substituted with quinolinyl, morpholinyl or with pyrrolidinonyl; —CO—$Ar^2$; or Q is a radical of formula

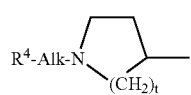

wherein t is 2; $R^4$ is amino, mono- or di($C_{1-6}$alkyl)amino.
(b) Q is $C_{1-6}$alkyl substituted with one or two $Ar^2$ radicals; $C_{1-6}$alkyl substituted with quinolinyl, morpholinyl or with pyrrolidinonyl;

(c) Q is —CO—$Ar^2$; or
(d) Q is a radical of formula (a) wherein t is 2; $R^4$ is amino, mono- or di($C_{1-6}$alkyl)amino.
(e) Q is hydrogen.

Subgroups III of the compounds of formula (I) are those compounds of formula (I), or any subgroup of compounds of formula (I) specified herein, such as the subgroups I and II mentioned above, wherein
(a) $R^1$ and/or $R^2$ are $Ar^2$, —CO—$Ar^2$ or a heterocycle selected from piperidinyl, piperazinyl, morpholinyl, thiomorpholinyl, pyridyl, pyrazinyl, pyrimidinyl, furanyl, tetrahydrofuranyl, thienyl, pyrrolyl, thiazolyl, oxazolyl, imidazolyl, quinolinyl, quinoxalinyl, benzofuranyl, benzothienyl, benzimidazolyl, benzoxazolyl, benzthiazolyl wherein each of said heterocycles may optionally be substituted with 1, 2, or 3 substituents each independently selected from halo, hydroxy, amino, cyano, carboxyl, $C_{1-6}$alkyl, $C_{1-6}$alkyloxy, $C_{1-6}$alkyloxy$C_{1-6}$alkyl, hydroxy$C_{1-6}$alkyl, mono- or di($C_{1-6}$alkyl)amino; or wherein
(b) $R^1$ and/or $R^2$ are $Ar^2$, —CO—$Ar^2$, or a heterocycle selected from morpholinyl, pyridyl, pyrazinyl, pyrimidinyl, furanyl, tetrahydrofuranyl, thienyl, thiazolyl, oxazolyl, imidazolyl and quinolinyl; wherein each of said heterocycles may optionally be substituted with 1 or 2 substituents independently selected from halo, hydroxy, amino, cyano, $C_{1-6}$alkyl and $C_{1-6}$alkyloxy; or wherein
(c) $R^1$ and/or $R^2$ are $Ar^2$, —CO—$Ar^2$, morpholinyl, pyridyl or quinolinyl; wherein each of said heterocycles may optionally be substituted with 1 or 2 substituents independently selected from hydroxy and $C_{1-6}$alkyl; or wherein
(d) $R^1$ and/or $R^2$ are $Ar^2$, —CO—$Ar^2$, morpholinyl or quinolinyl.

Subgroups IV of the compounds of formula (I) are those compounds of formula (I), or any subgroup of compounds of formula (I) specified herein, such as the subgroups I, II and III mentioned above, wherein $R^2$ is hydrogen.

Subgroups V of the compounds of formula (I) are those compounds of formula (I), or any subgroup of compounds of formula (I) specified herein, such as the subgroups I, II, III and IV mentioned above, wherein
(a) $R^3$ is hydrogen and Q is other than hydrogen;
(b) $R^3$ is a radical of formula:

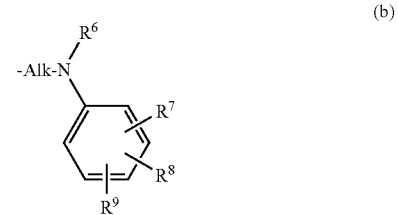

wherein
$R^6$ is selected from hydrogen, $C_{1-6}$alkyl, $Ar^2C_{1-6}$alkyl, hydroxy$C_{1-6}$alkyl, ($C_{1-6}$alkyloxy)$C_{1-6}$alkyl, amino$C_{1-6}$alkyl, carboxyl$C_{1-6}$alkyl, aminocarbonyl$C_{1-6}$alkyl;
$R^7$, $R^8$, $R^9$ independently from one another are selected from halo, cyano, $C_{1-6}$alkyl, cyano$C_{1-6}$alkyl, $R^{10a}$—O—, —N($R^{5a}R^{5b}$), trifluoromethyl, $R^{10a}$—O—C(=O)—, N($R^{5a}R^{5b}$)—C(=O)—, $R^{10a}$—O—C$_{1-6}$alkyl, N($R^{5a}R^{5b}$)—C$_{1-6}$alkyl, $R^{10a}$—O—C(=O)—C$_{1-6}$alkyl, N($R^{5a}R^{5b}$)—C(=O)—C$_{1-6}$alkyl, $R^{10b}$—C(=O)—O—, $R^{10b}$—C(=O)—O—C$_{1-6}$alkyl; and $R^8$ and/or $R^9$ may also be hydrogen;

each $R^{5a}$ and $R^{5b}$ independently from each other are hydrogen or $C_{1-6}$alkyl;
$R^{10a}$ is hydrogen or $C_{1-6}$alkyl;
$R^{10b}$ is $C_{1-6}$alkyl; or wherein (c) $R^3$ is a radical of formula (b) wherein
$R^6$ is selected from hydrogen, $C_{1-6}$alkyl, hydroxy$C_{1-6}$alkyl, amino$C_{1-6}$alkyl, carboxyl$C_{1-6}$alkyl and aminocarbonyl$C_{1-6}$alkyl;
$R^7$, $R^8$, $R^9$ independently from one another are selected from halo, cyano, $C_{1-6}$alkyl, cyano$C_{1-6}$alkyl, $R^{10a}$—O—, —N($R^{5a}$,$R^{5b}$) $R^{10a}$—O—C(=O)—, N($R^{5a}R^{5b}$)—C(=O)—, $R^{10a}$—O—$C_{1-6}$alkyl, N($R^{5a}R^{5b}$)—$C_{1-6}$alkyl, $R^{10a}$—O—C(=O)—$C_{1-6}$alkyl, N($R^{5a}R^{5b}$)—C(=O)—$C_{1-6}$alkyl, $R^{10b}$—C(=O)—O—$C_{1-6}$alkyl; and $R^8$and/or $R^9$ may also be hydrogen;
each $R^{5a}$ and $R^{5b}$ independently from each other are hydrogen or $C_{1-6}$alkyl;
$R^{10a}$ is hydrogen or $C_{1-6}$alkyl;
$R^{10b}$ is $C_{1-6}$alkyl; or (d) $R^3$ is a radical of formula (b) wherein
$R^6$ is selected from hydrogen, hydroxy$C_{1-6}$alkyl, amino$C_{1-6}$alkyl and aminocarbonyl$C_{1-6}$alkyl;
$R^7$, $R^8$, $R^9$ independently from one another are selected from halo, $C_{1-6}$alkyl, cyano$C_{1-6}$alkyl, $R^{10a}$—O—, —N($R^{5a}R^{5b}$), $R^{10a}$—O—$C_{1-6}$alkyl, N($R^{5a}R^{5b}$)—$C_{1-6}$alkyl, $R^{10a}$—O—C(=O)—$C_{1-6}$alkyl, $R^{10b}$—C(=O)—O—$C_{1-6}$alkyl; and $R^8$ and/or $R^9$ may also be hydrogen;
$R^{5a}$ and $R^{5b}$ are hydrogen;
$R^{10a}$ is hydrogen or $C_{1-6}$alkyl;
$R^{10b}$ is $C_{1-6}$alkyl; or (e) $R^3$ is a radical of formula (b) wherein
$R^6$ is hydrogen;
$R^7$, $R^8$, $R^9$ independently from one another are selected from $C_{1-6}$alkyl,
$R^{10a}$—O—$C_{1-6}$alkyl, and $R^8$ and/or $R^9$ may also be hydrogen;
$R^{5a}$ and $R^{5b}$ are hydrogen;
$R^{10a}$ is hydrogen or $C_{1-6}$alkyl; and wherein in case of restrictions (b), (c) and (d), Q is hydrogen.

Subgroups VI of the compounds of formula (I) are those compounds of formula (I), or any subgroup of compounds of formula (I) specified herein, such as the subgroups I, II, III, IV and V mentioned above, wherein $Ar^1$ is phenyl or phenyl substituted with 1, 2 or 3 substituents selected from halo, hydroxy, $C_{1-6}$alkyl, hydroxy$C_{1-6}$alkyl, $CF_3$ and $C_{1-6}$alkyloxy;

Subgroups VII of the compounds of formula (I) are those compounds of formula (I), or any subgroup of compounds of formula (I) specified herein, such as the subgroups I, II, III, IV, V and VI mentioned above, wherein $Ar^2$ is phenyl or phenyl substituted with 1, 2 or 3 substituents selected from halo, hydroxy, $C_{1-6}$alkyl, cyano, nitro, hydroxyl-$C_{1-6}$alkyl, $CF_3$, $C_{1-6}$alkyloxy, hydroxy$C_{1-6}$alkyloxy, $C_{1-6}$alkyloxycarbonyl, phenyl and phenoxy.

Preferred compounds are any of the compounds listed in tables 1 and 2, more in particular the compound numbers 1-7, 57.

The compounds of formula (I) can be prepared by N-alkylation or in some instances by N-acylation reactions, as outlined in the following reaction schemes wherein Q, Alk, $R^1$, $R^2$, $R^3$, $R^4$ have the meanings specified in relation to the compounds of formula (I) or any of the subgroups of compounds of formula (I). W represents a leaving group such as tosyl, mesyl, halo, in particular chloro or bromo. These N-alkylation reactions are typically conducted in a suitable solvent such as an ether, e.g. THF, dioxane, a halogenated hydrocarbon, e.g. dichloromethane, $CHCl_3$, toluene, a polar aprotic solvent such as DMF, DMSO, DMA, HMPT, NMP, acetonitrile and the like. A base may be added to pick up the acid that is liberated during the reaction, e.g. an alkali metal carbonate or hydrogen carbonate, a trialkylamine such as triethylamine, or, if desired, stronger bases such as alkali metal hydrides, e.g. NaH. If desired, certain catalysts such as iodide salts (e.g. KI) may be added.

The compounds of formula (I) can be prepared by N-alkylating a benzimidazole (II) with an alkylating agent (III) as outlined in the following reaction scheme.

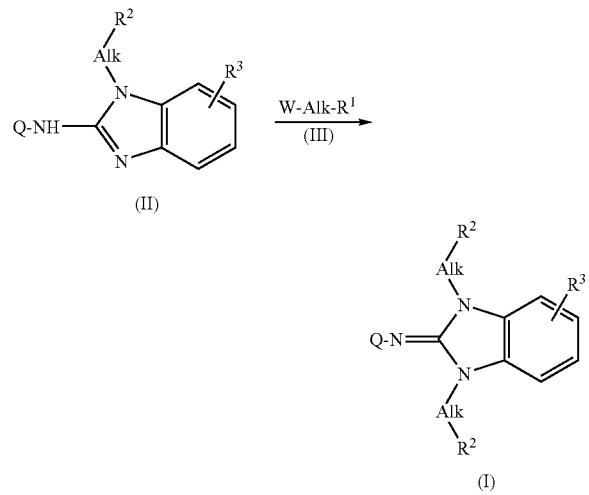

The compounds of formula (I) can also be prepared by N-alkylating or N-acylating (where Q is $Ar^2$—CO—) a benzimidazole (IV) with an alkylating or acylating agent (V) as outlined in the following reaction scheme.

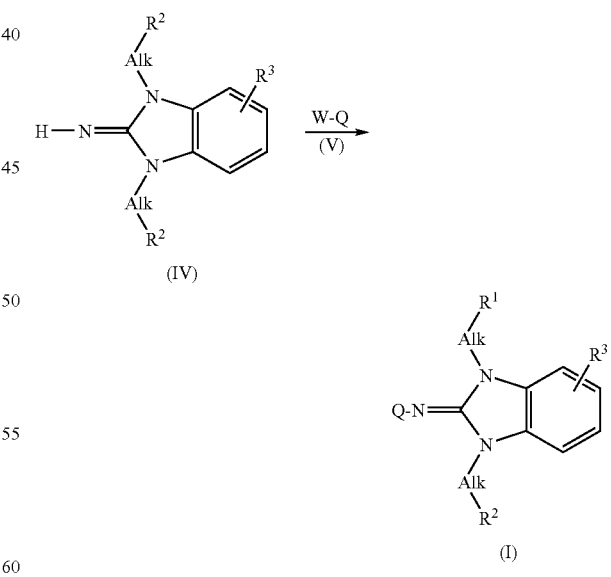

Compounds of formula (I) wherein $R^3$ is a radical (b) wherein the group Alk is methylene, which compounds can be represented by formula (I-a) can be prepared starting from intermediates of formula (VI) wherein $R^{11}$ is $C_{1-6}$alkyl, in particular methyl or ethyl, by a reduction reaction, e.g. with $LiAlH_4$, to intermediates (VII) having a hydroxymethylene group. The latter group can be oxidized to an aldehyde group (intermediates VIII) with a mild oxidant, e.g. with MnO$_2$, which can further be derivatized with amines, e.g. with a reductive amination process, to the desired compounds of formula (I-a).

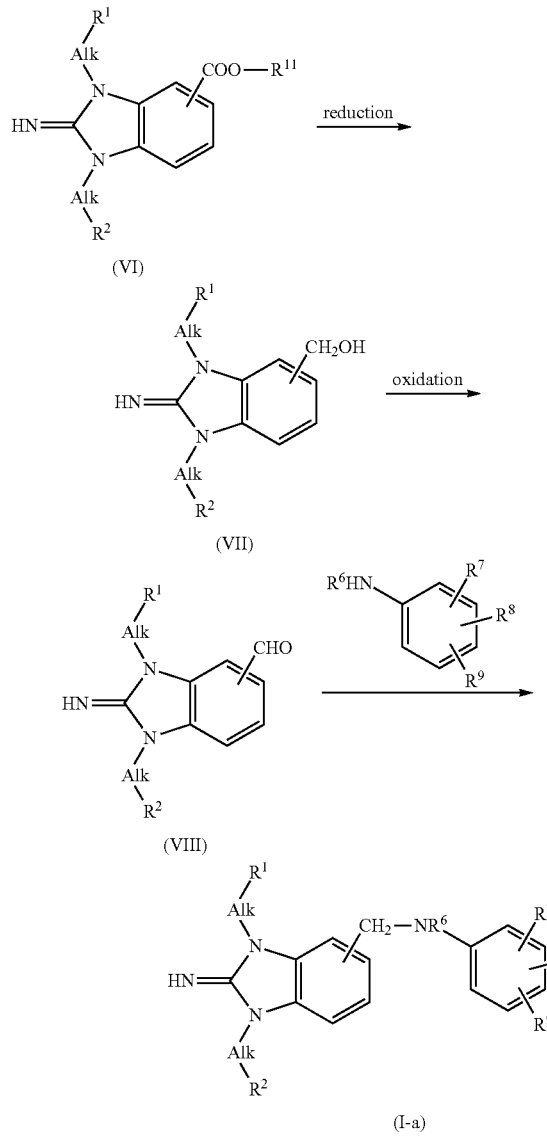

Compounds of formula (I) wherein Q is a radical (a), which compounds can be represented by formula (I-b) can be prepared by N-alkylating intermediates of formula (IX) with a reagent R$^4$-Alk-W using the same reaction conditions as described above for the N-alkylation reactions.

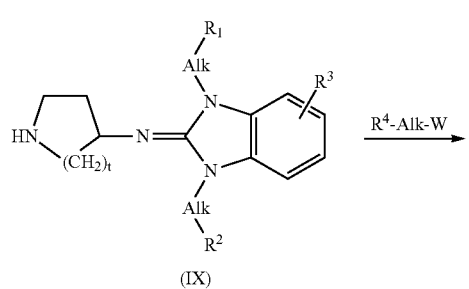

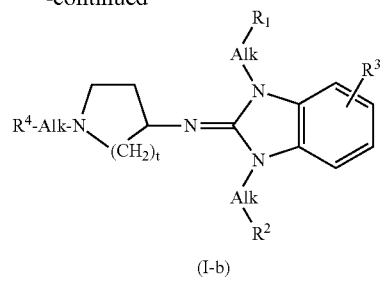

Compounds of formula (I) may be converted into each other following art-known functional group transformation reactions, comprising those described hereinafter.

Nitro groups can be reduced to amino groups, which subsequently may be alkylated to mono- or dialkylamino groups, or acylated to arylcarbonylamino or alkylcarbonylamino and the like groups. Cyano groups may be reduced to aminomethylene groups, which similarly may be derivatized.

A number of the intermediates used to prepare the compounds of formula (I) are known compounds or are analogs of known compounds which can be prepared following modifications of art-known methodologies readily accessible to the skilled person. A number of preparations of intermediates are given hereafter in somewhat more detail. In the following reaction schemes the radicals Q, R$^1$, R$^2$, R$^3$ have the meanings specified in relation to the compounds of formula (I) or any of the subgroups of compounds of formula (I). W represents a leaving group such as tosyl, mesyl, halo, in particular chloro or bromo.

Intermediates of formula (II) can be prepared as outlined in the following scheme:

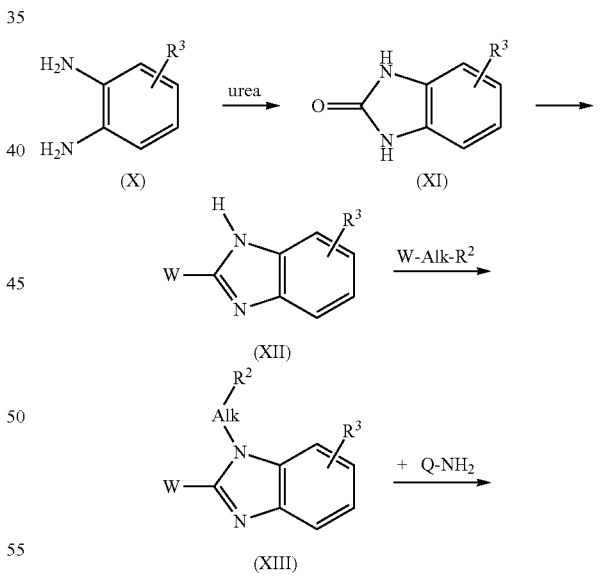

In a first step, a diaminobenzene (X) is cyclized with urea in a suitable solvent, e.g. xylene, to yield a benzimidazolone (XI). The latter is converted to a benzimidazole derivative (XII) wherein W is a leaving group as specified above, in particular by reaction of (XI) with a suitable halogenating agent, for example POCl$_3$, and the resulting intermediate (XIII) is reacted with a amine derivative Q-NH$_2$ to obtain intermediates of formula (II). The latter can alternatively be prepared as follows:

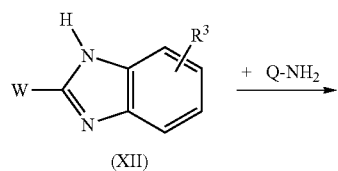
(XII)

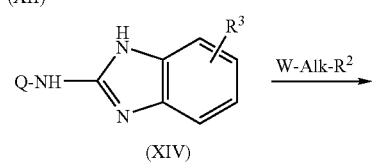
(XIV)

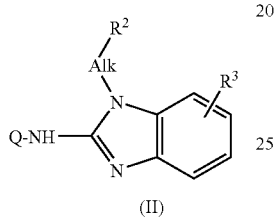
(II)

Intermediates (XII) are reacted with a amine derivative Q-NH$_2$ to obtain intermediates of formula (XIV), which in turn are reacted with a reagent W-Alk-R$^2$ thus obtained intermediates (II).

Intermediates of formula (IV) can be prepared as outlined in the following scheme:

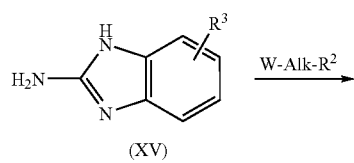
(XV)

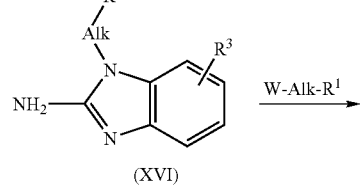
(XVI)

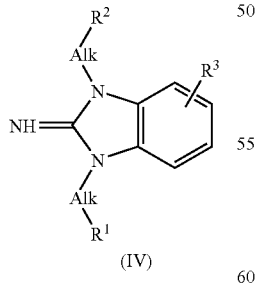
(IV)

First the 2-aminobenzimidazole derivatives (XV) are N-alkylated with a reagent W-Alk-R$^2$, thus yielding intermediates (XVI), which are subsequently alkylated to yield the desired intermediates of formula (IV). The N-alkylation reactions can be conducted following the same procedures as described above for the alkylations of (II) or (IV) to obtain compounds (I). The intermediates (XVI) can also be prepared by first alkylating intermediates (X) to obtain intermediates (XVII) which are cyclized with cyanogen bromide to intermediates (XVI):

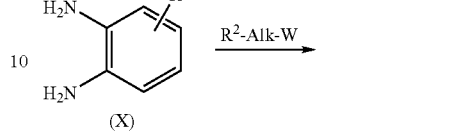
(X)

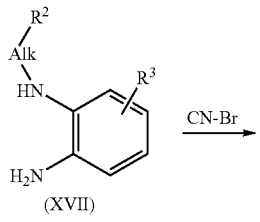
(XVII)

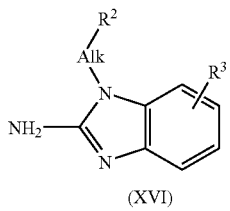
(XVI)

The intermediates of formula (VI) may be prepared as follows:

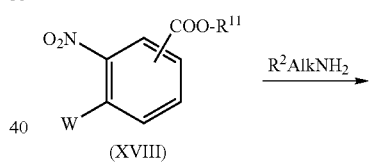
(XVIII)

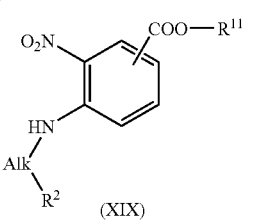
(XIX)

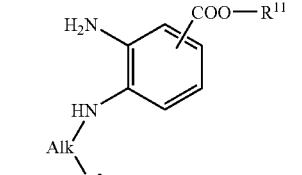
(XX)

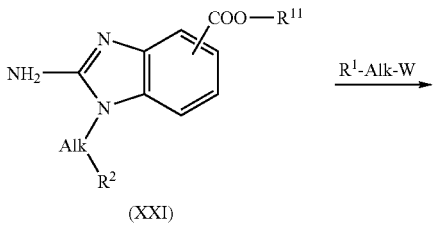
(XXI)

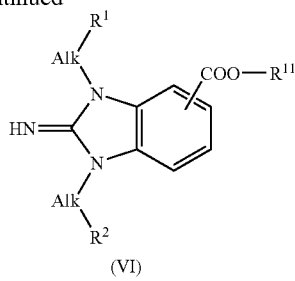

(VI)

The nitrobenzene derivative (XVIII) is reacted with $R^2$-Alk—$NH_2$ to intermediate (XIX) wherein the nitro group is reduced, e.g. with Raney Nickel to yield intermediates (XX) which are cyclized with cyanogens bromide to the 2-aminobenzimidazoles (XXI). The latter in turn are N-alkylated thus obtaining intermediates (VI).

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers, which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, compounds of the invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof, the addition salts or stereochemically isomeric forms thereof are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any subgroup thereof in the manufacture of a medicament for the treatment or the prevention of viral infections, particularly RSV infection.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

EXAMPLES

The following examples are intended to illustrate the present invention.

The compounds were analysed by LC/MS using one of the following methods:

LCT: electrospray ionisation in positive mode, scanning mode from 100 to 900 amu; Xterra MS C18 (Waters, Milford, Mass.) 5 µm, 3.9×150 mm); flow rate 1 ml/min. Two mobile phases (mobile phase A: 85% 6.5 mM ammonium acetate +15% acetonitrile; mobile phase B: 20% 6.5 mM ammonium acetate +80% acetonitrile) were employed to run a gradient from 100% A for 3 min to 100% B in 5 min., 100% B for 6 min to 100% A in 3 min, and equilibrate again with 100% A for 3 min).

ZQ: electrospray ionisation in both positive and negative (pulsed) mode scanning from 100 to 1000 amu; Xterra RP C18 (Waters, Milford, Mass.) 5 µm, 3.9×150 mm); flow rate 1 ml/min. Two mobile phases (mobile phase A: 85% 6.5mM ammonium acetate+15% acetonitrile; mobile phase B: 20% 6.5 mM ammonium acetate+80% acetonitrile) were employed to run a gradient condition from 100% A for 3 min to 100% B in 5 min., 100% B for 6 min to 100% A in 3 min, and equilibrate again with 100% A for 3 min).

The numbers of the end products in the following examples (compound 1 etc.) correspond to the compound numbers in Tables 1 to 5.

Example 1

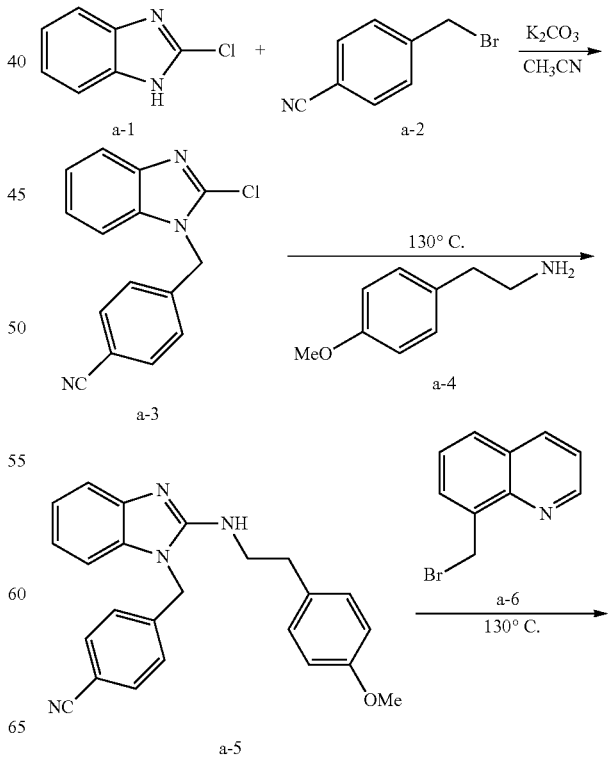

Scheme A

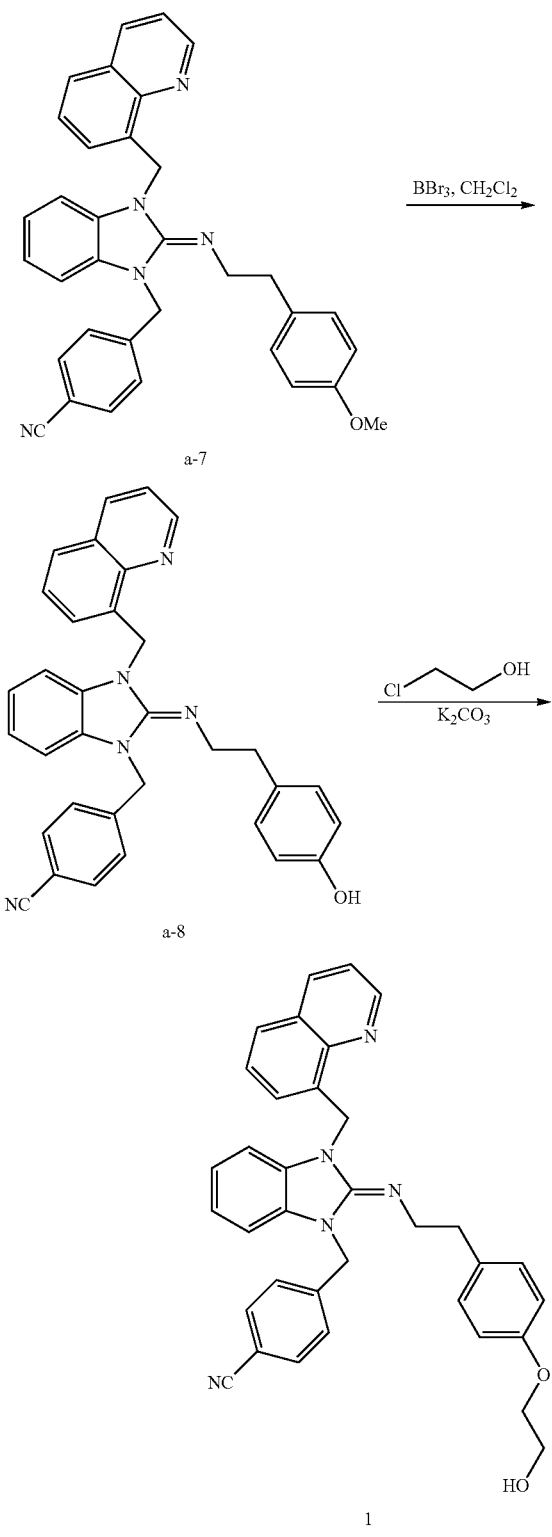

Preparation of Intermediate a-3

A mixture of a-1 (11.7 g, 0.076 mol), a-2 (7.5 g, 0.076 mol) and potassium carbonate (15.9 g, 0.11 mol) in acetonitrile (280 ml) was heated to reflux for 4 h. The reaction mixture was cooled down to room temperature, and water was added. The product was extracted three times with CH$_2$Cl$_2$. The combined organic extracts were dried over MgSO$_4$, and the solvent was removed under reduced pressure to give a-3 in quantitative yield.

Preparation of Intermediate a-5

A mixture of a-3 (10 g, 0.037 mol), and a-4 (5.7 g, 0.037 mol) was heated to 130° C. for 4 h. The reaction flask was then cooled to room temperature. H$_2$O was added, and the product was extracted with CH$_2$Cl$_2$. The combined organic extracts were dried over MgSO$_4$, and purification of the concentrated filtrate by column chromatography (Silica gel, CH$_2$Cl$_2$/MeOH/NH$_4$OH; 97/3/0.5) afforded 3.6 g of a-5 (26%).

Preparation of Intermediate a-7

A mixture of a-5 (4.00 g, 0.01 mol), and a-6 (2.3 g, 0.01 mol) was heated to 130° C. for 3 h. The reaction flask was then cooled to room temperature. H$_2$O was added, and the product was extracted with CH$_2$Cl$_2$. The combined organic extracts were dried over MgSO$_4$, and purification of the concentrated filtrate by column chromatography (Silica gel, CH$_2$Cl$_2$/MeOH/NH$_4$OH; 94/6/0.5) gave 1.8 g of a-7 (33%).

Preparation of Intermediate a-8 a-7 (1.4 g, 0.0027 mol) was dissolved in 70 ml of CH$_2$Cl$_2$. The solution was then cooled to 0° C., and a solution of BBr$_3$ (1 M in CH$_2$Cl$_2$, 10.7 ml, 0.011) was added. The mixture was further stirred at room temperature for 1 h and then quenched with water. Usual work-up gave rise to a-8 in quantitative yield.

Preparation of Final Compound 1

A mixture of a-8 (0.5 g, 0.001 mol), 2-chloroethanol (0.1 ml, 0.0015 mol), K$_2$CO$_3$ (0.17 g, 0.0012mol) in dry DMF (5 ml) was heated to 80° C. for 72 h, after which, it was cooled to room temperature. Extraction with ethyl acetate, followed by column chromatography (Silica gel, CH$_2$Cl$_2$/MeOH/NH$_4$OH; 95/5/0.5) gave rise to 130 mg of compound 1 (24%).

Example 2

Scheme B

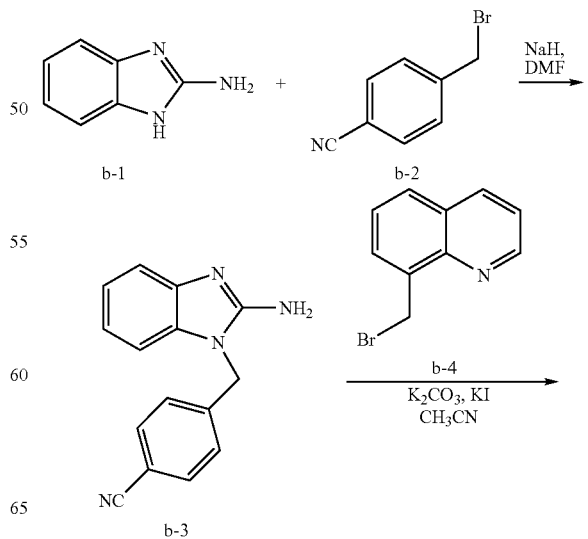

21
-continued

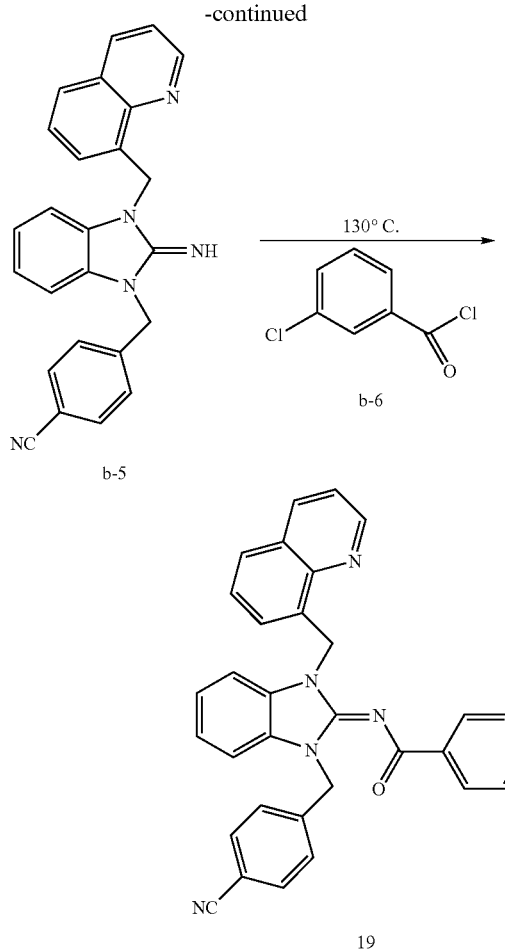

22 trate by column chromatography (Silica gel, CH$_2$Cl$_2$/MeOH/ NH$_4$OH; 99/1/0.1) afforded 0.25 g of compound 19 (85%, melting point: 160° C.).

Example 3

Scheme C

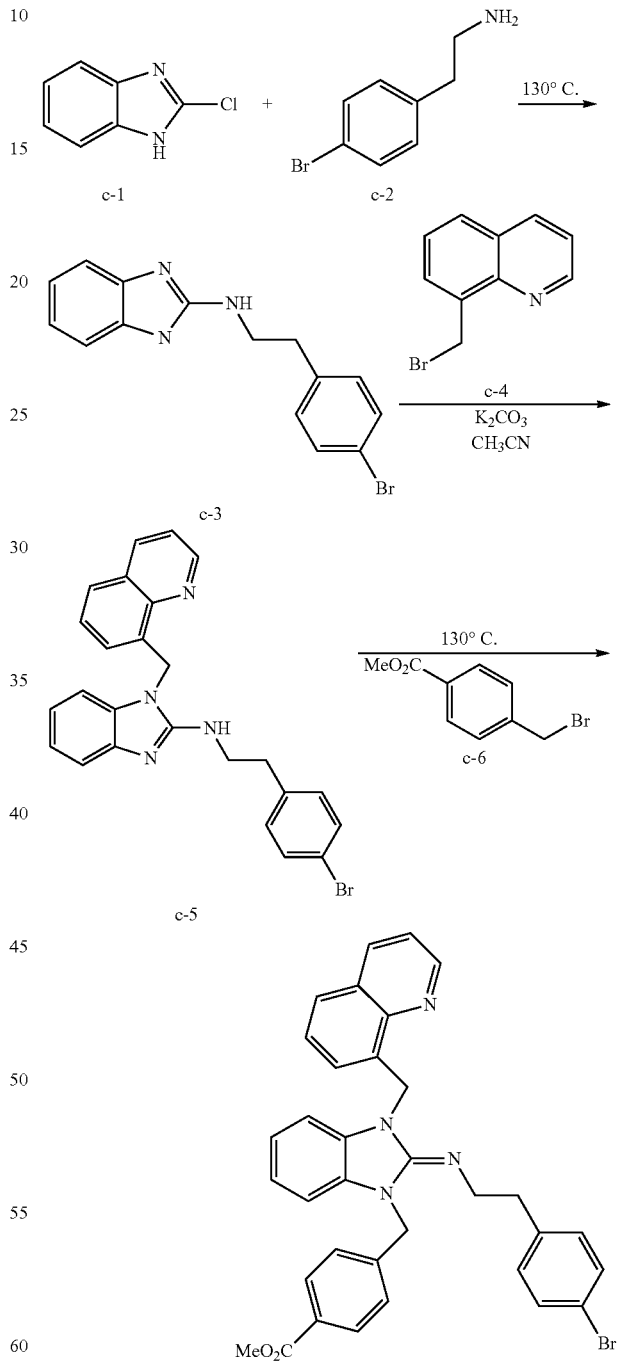

Preparation of Intermediate b-3

NaH (60% mineral oil, 6 g, 0.15 mol) was added portion wise to a solution of b-1(20 g, 0.15 mol) in DMF (100 ml) under N$_2$. The reaction mixture was stirred for 1 h, and then b-2 (14.7 g, 0.075 mol) was added portion wise, and stirring was continued further for 2 h. The mixture was poured into a mixture of ice and water, and the product was extracted with ethyl acetate. The combined organic extracts were dried over MgSO$_4$, and purification of the concentrated filtrate by column chromatography (Silica gel, CH$_2$Cl$_2$/MeOH/NH$_4$OH; 95/5/0.5) afforded 14 g of b-3 (38%, melting point: 221° C.).

Preparation of Intermediate b-5

A mixture of b-3 (13 g, 0.052 mol), b-4 (11.6 g, 0.052 mol), potassium carbonate (10.8 g, 0.078 mol) and a catalytic amount of KI in acetonitrile (600 ml) was heated to reflux for 12 h. The reaction mixture was cooled down to room temperature, and water was added. The product was extracted three times with CH$_2$Cl$_2$. The combined organic extracts were dried over MgSO$_4$, and the solvent was removed under reduced pressure to give b-5. Purification by column chromatography (Silica gel, Toluene/Isopropanol/NH$_4$OH; 85/15/1) gave 6.5 g of b-5 (32%).

Preparation of Final Compound 19

A mixture of b-5 (0.3 g, 0.0008 mol), and b-6 (0.4 g, 0.0023 mol) was heated to 130° C. for 4 h. The reaction flask was then cooled to room temperature. H$_2$O was added, and the product was extracted with CH$_2$Cl$_2$. The combined organic extracts were washed with an aqueous solution of K$_2$CO$_3$ (10%), and then dried over MgSO$_4$. Purification of the concentrated fil- Preparation of Intermediate c-3

A mixture of c-1 (5.00 g, 0.033 mol), and c-2 (13.13 g, 0.066 mol) was heated to 130° C. for 4 h. The reaction flask was then cooled to room temperature. H$_2$O was added, and the product was extracted with CH$_2$Cl$_2$. The combined organic extracts were dried over MgSO$_4$, and purification of the concentrated filtrate by column chromatography (Silica gel, CH$_2$Cl$_2$/MeOH/NH$_4$OH; 97/3/0.1) afforded 11.5 g of c-3 (92%).

Preparation of Intermediate c-5

A mixture of c-3 (11.0 g, 0.035 mol), c-4 (7.75 g, 0.035 mol) and potassium carbonate (7.21 g, 0.052 mol) in acetonitrile (165 ml) was heated to reflux for 12 h. The reaction mixture was cooled down to room temperature, and water was added. The product was extracted three times with Ethylacetate. The combined organic extracts were dried over MgSO$_4$, and purification of the concentrated filtrate by column chromatography (Silica gel, CH$_2$Cl$_2$/MeOH; 98/2) gave rise to 9.78 g of c-5 (61%).

Preparation of Final Compound 35

A mixture of c-5 (0.5 g, 0.0011 mol), and c-6 (0.75 g, 0.0033 mol) was heated to 130° C. for 2 h. The reaction flask was then cooled to room temperature. H$_2$O was added, and the product was extracted with CH$_2$Cl$_2$. The combined organic extracts were dried over MgSO$_4$, and purification of the concentrated filtrate by column chromatography (Silica gel, CH$_2$Cl$_2$/MeOH/NH$_4$OH; 93/7/0.1) afforded 3.6 g of compound 35 (23%, melting point: 128 ° C.).

Example 4

Scheme D

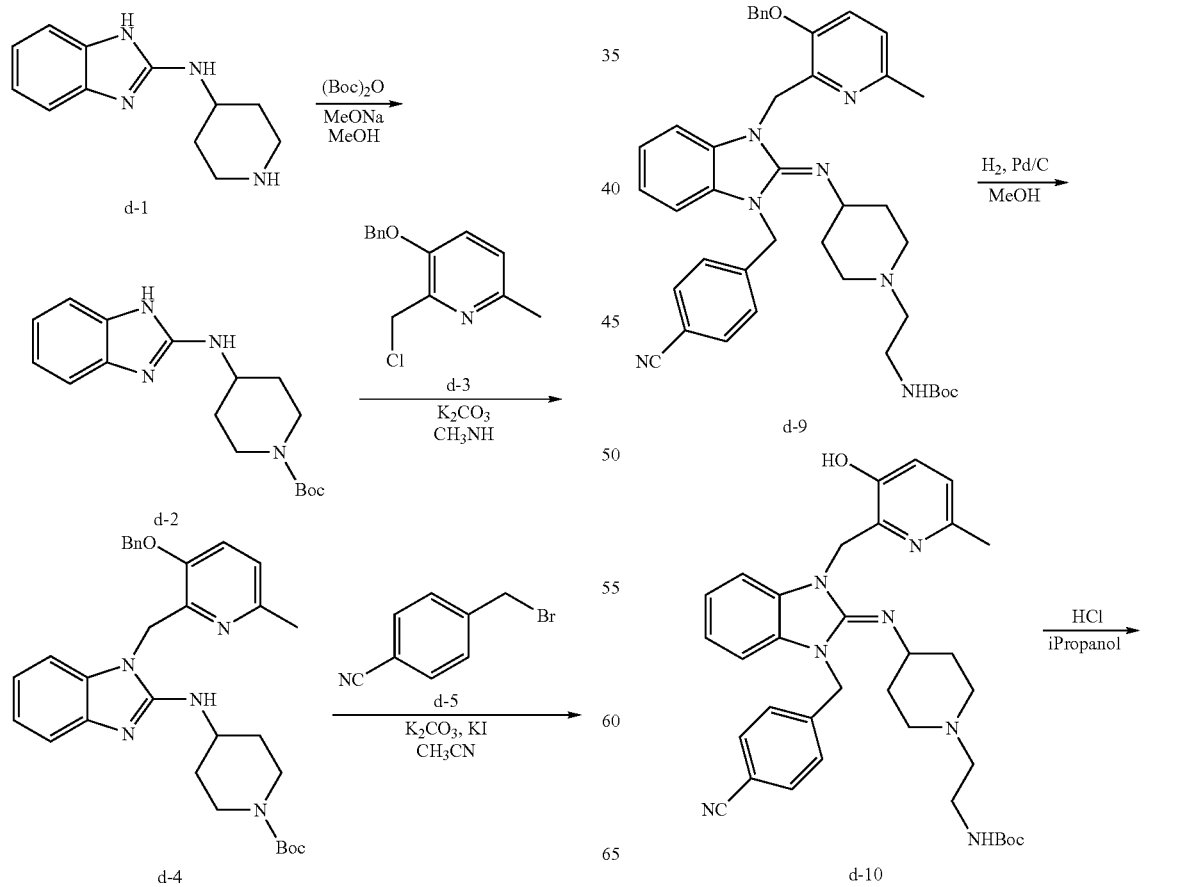

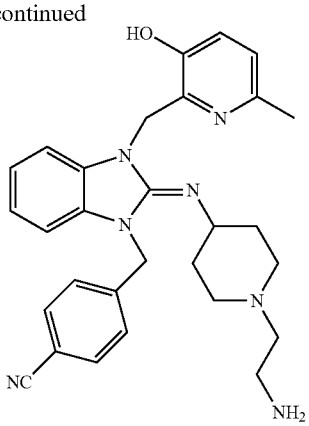

55

Preparation of Intermediate d-2

MeONa (66 ml of a 30% sol in MeOH, 0.34 mol) was added to a mixture of d-1 (52 g, 0.17 mol) in MeOH (500 ml) at 5° C. and stirred for 2 h at that temperature. (Boc)₂O (41 g, 0.17 mol) was then added at the same temperature and stirred at room temperature overnight. The mixture was evaporated and suspended in water/diisopropylether. The residue was filtered off, washed with water/diisopropylether and dried to yield 40 g of d-2 (73%).

Preparation of Intermediate d-4

A mixture of d-2 (5 g, 0.0158 mol), d-3 (4.5 g, 0.0158 mol) and K₂CO₃ (5.4 g, 0.039 mol) in acetonitrile (100 ml) was refluxed for 12 h. The solvent was evaporated to dryness. The compound was extracted with CH₂Cl₂. The organic layer was dried over MgSO₄, filtered, and the solvent was evaporated giving rise to 9 g of d-4 (100%).

Preparation of Intermediate d-6

A mixture of d-4 (7.9 g, 0.015 mol), d-5 (2.9 g, 0.015 mol), K₂CO₃ (3.1 g, 0.022 mol) and KI (catalytic amount) in acetonitrile (150 ml) was refluxed for 6 h, then cooled to room temperature and the solvent was evaporated to dryness. The residue was dissolved in CH₂Cl₂. The organic layer was washed with H₂O, dried (over MgSO4), filtered, and the solvent was evaporated. The residue (10.6 g) was purified by column chromatography (silica gel, CH₂Cl₂/CH₃OH/ NH₄OH, 92/8/0.5) to afford 3 g of d-4 (31%).

Preparation of Intermediate d-7

A mixture of d-6 (2.3 g, 0.0035 mol), HCl (20 ml of a 5 N sol in isopropanol) in isopropanol (20 ml) was stirred at 60° C. for 1 h. The solvent was evaporated to dryness. The residue was dissolved in Et₂O. The precipitate was filtered off and dried to give 3 g of the title compound in quantitative yield. The compound was used further without purification.

Preparation of Intermediate d-9

A mixture of d-7 (2.08 g, 0.0035 mol), d-8 (1.2 g, 0.0053 mol) and K₂CO₃ (2.0 g, 0.0143 mol) in acetonitrile (100 ml) was stirred at room temperature for 2 h, and then refluxed for 24 h. The solvent was evaporated to dryness. The residue was dissolved in CH₂Cl₂. The organic layer was washed with H₂O, dried (over MgSO4), filtered, and the solvent was evaporated. The residue (2.3 g) was purified by column chromatography (silica gel, CH₂Cl₂/CH₃OH/NH₄OH, 90/10/1) to give 0.61 g of d-9 (25%).

Preparation of Intermediate d-10

A mixture of d-9 (0.6 g, 0.0009 mol) and Pd/C (0.2 g, 10%) in MeOH (15 ml) was hydrogenated at atmospheric pressure for 30 min, and then filtered over Celite. Celite was washed with CH₃OH, and the filtrate was evaporated to give rise to 0.5 g of d-10 (96%). The compound was used further without purification.

Preparation of Final Compound 55

A mixture of d-10 (0.5 g, 0.0008 mol), HCl (5 ml of a 5 N sol in isopropanol) in isopropanol (25 ml) was stirred at 60° C. for 6 h, then cooled to room temperature. The hot precipitate was filtered, washed with isopropanol, then with diethyl ether and dried. This fraction was dissolved in H₂O, basified with NH₄OH and extracted with CH₂Cl₂/CH₃OH. The organic layer was washed with H₂O, dried (over MgSO4), filtered, and the solvent was evaporated. Crystallization from CH₃CN/EtOH yielded 0.29 g of compound 55 (70%, melting point: 212° C.).

Example 5

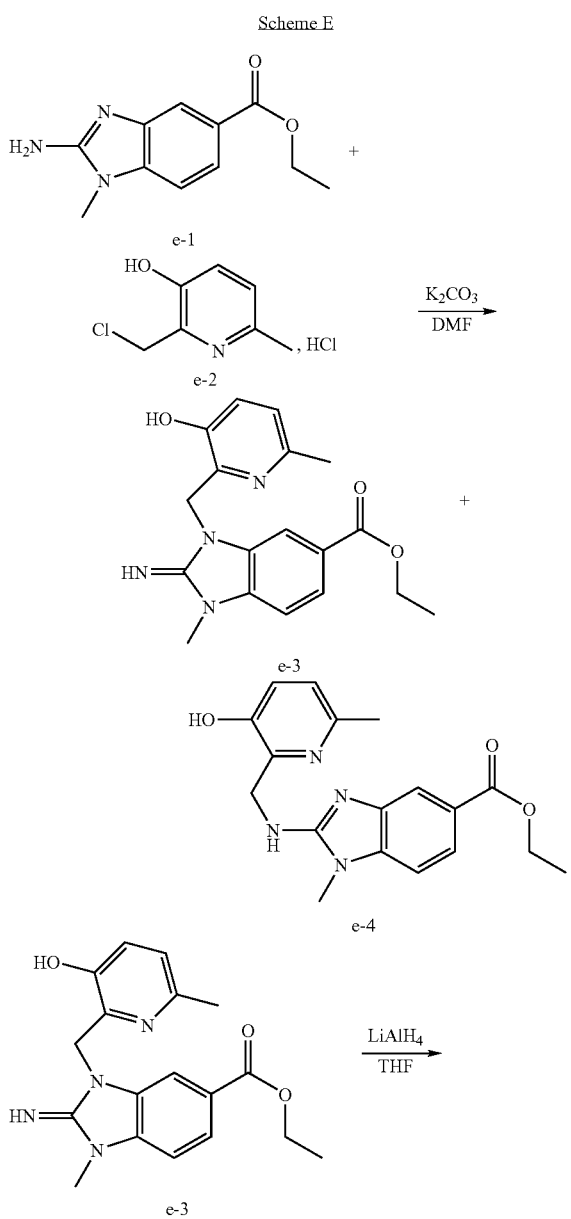

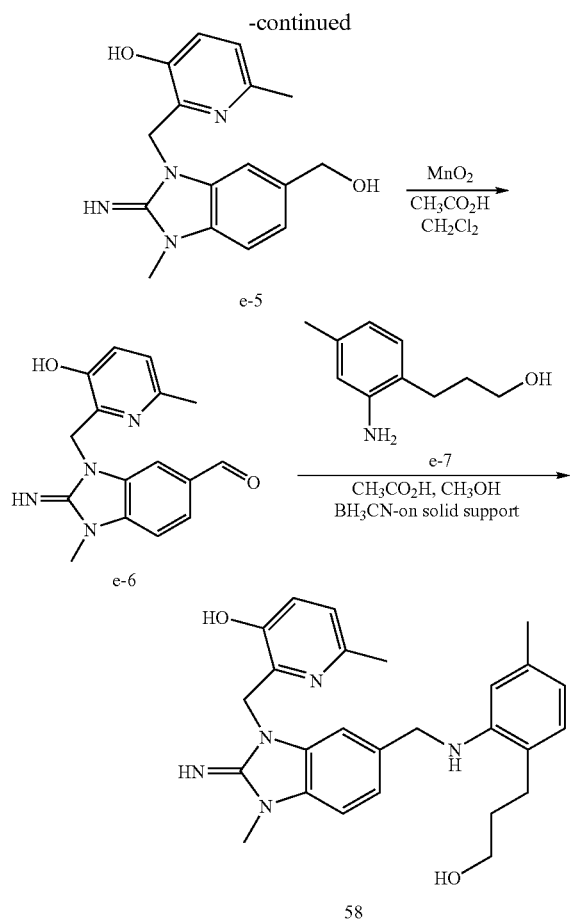

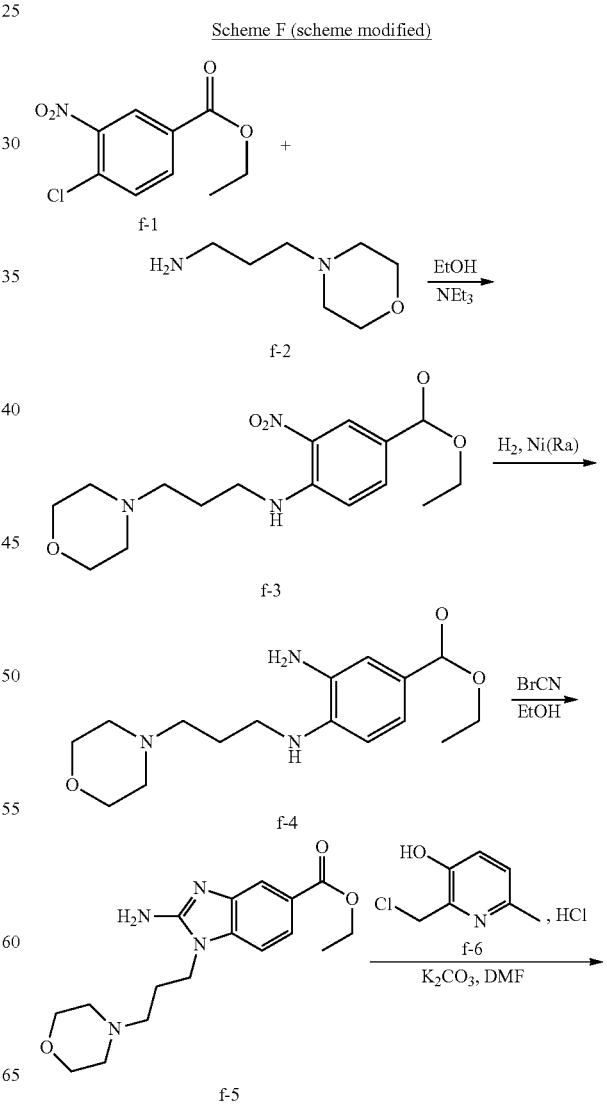

CH$_3$OH (20 ml). The mixture was stirred at room temperature for 2 hours, and then filtered over celite. Celite was washed with CH$_2$Cl$_2$/CH$_3$OH. The filtrate was evaporated, yielding 0.6 g of e-6 (CH$_3$CO$_2$H salt, 100%). This product was used directly in the next reaction step.

Preparation of Final Compound 58

CH$_3$CO$_2$H (4 drops) then BH$_3$CN— on solid support (0.0013 mol) were added to a mixture of e-6 (0.0007 mol) and e-7 (0.001 mol) in CH$_3$OH (12 ml). The mixture was stirred at room temperature for 48 hours, and then filtered. The solid support was washed with CH$_2$Cl$_2$/CH$_3$OH. The filtrate was evaporated. The residue (0.35 g) was purified by column chromatography over silica gel (eluent: CH$_2$Cl$_2$/CH$_3$OH/NH$_4$OH; 90/10/0.5; 10 μm). The pure fractions were collected and the solvent was evaporated. The residue (0.067 g) was crystallized from 2-propanone. The precipitate was filtered off and dried, yielding 0.054 g of compound 58 (17%, melting point: 195° C.).

Example 6

Preparation of Intermediate e-3

A mixture of e-1 (0.0114 mol), e-2 (0.0114 mol) and K$_2$CO$_3$ (0.0399 mol) in DMF (50 ml) was stirred at 70° C. for 2 hours. The precipitate was filtered. The filtrate was evaporated. The residue was taken up in CH$_2$Cl$_2$/CH$_3$OH. The organic layer was washed twice with H$_2$O, dried (over MgSO$_4$), filtered and the solvent was evaporated to dryness. The residue (5.1 g) was crystallized from 2-propanone. The precipitate was filtered off and dried. The mother layer (3.1 g) was purified by column chromatography over silica gel (eluent: CH$_2$Cl$_2$/CH$_3$OH/NH$_4$OH 90/10/0.5; 10 μm). Two fractions were collected and the solvent was evaporated. Yield: 1.4 g of e-4 (36%) and 1.2 g of e-3 (31%). Part of e-4 (0.2 g) was recrystallized from 2-propanone. The precipitate was filtered off and dried. Yield: 0.132 g of e-4 (melting point >250° C.). Part of e-3 (0.1 g) was recrystallized from 2-propanone. The precipitate was filtered off and dried, yielding 0.062 g of e-3 (melting point: 192° C.).

Preparation of Intermediate e-5

LiAlH$_4$ (0.007 mol) was added portion wise at 5° C. to a mixture of e-3 (0.0035 mol) in THF (30 ml) under N$_2$ flow. The mixture was stirred at 5° C. for 30 minutes, then stirred at room temperature for 2 hours, poured into H$_2$O and filtered over celite. Celite was washed with CH$_2$Cl$_2$/CH$_3$OH. The filtrate was evaporated. The residue (1.5 g) was taken up in HCl 1N. The mixture was washed with CH$_2$Cl$_2$, basified with NaOH 3N. The precipitate was filtered, washed with H$_2$O and dried with diethyl ether, yield: 0.5 g of e-5 (48%).

Preparation of Intermediate e-6

MnO2 (4.5 g) was added portion wise at room temperature to a mixture of e-5 (0.0015 mol) in CH$_3$CO$_2$H (0.5 ml) and

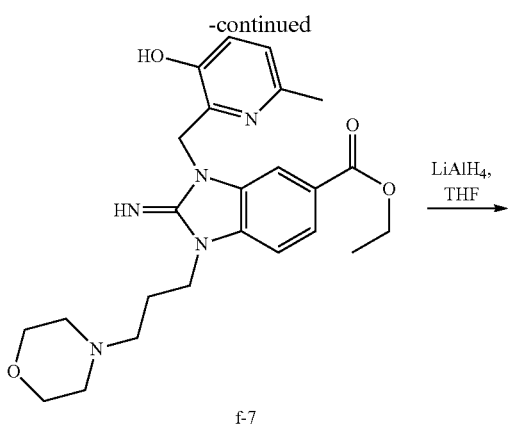

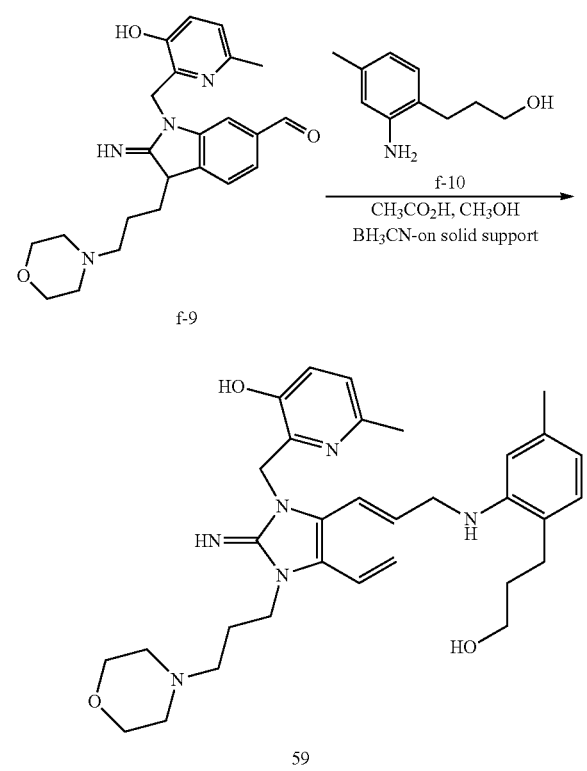

Preparation of Intermediate f-3

A mixture of f-1 (0.022 mol), f-2 (0.066 mol) and NEt₃ (0.066 mol) in C₂H₅OH (50 ml) was stirred at 60° C. for 12 hours, then evaporated to dryness and taken up in CH₂Cl₂. The organic layer was washed with H₂O, dried (over MgSO₄), filtered and the solvent was evaporated to dryness. Yield: 7.4 g of f-3 (100%).

Preparation of Intermediate f-4

A mixture of f-3 (0.022 mol) and Raney Nickel (15 g) in ethanol (110 ml) was hydrogenated at room temperature for 1 hour, and then filtered over celite. The filtrate was concentrated under reduced pressure. Yield: 7 g of f-4 (100%). The crude compound was used directly in the next reaction step.

Preparation of Intermediate f-5

A mixture of f-4 (0.022 mol) and BRCN (0.0242 mol) in C₂H₅OH (70 ml) was stirred and refluxed for 12 hours, then evaporated to dryness. The residue was taken up in CH₂Cl₂. The organic layer was washed with K₂CO₃ 10%, dried (over MgSO₄), filtered and the solvent was evaporated to dryness. The residue was crystallized from CH₃CN. The precipitate was filtered off and dried, yield: 2.4 g of f-5 (33%, melting point: 199° C.).

Preparation of Intermediate f-7

A mixture of f-5 (0.0009 mol), f-6 (0.0009 mol) and K₂CO₃ (0.0031 mol) in DMF (30 ml) was stirred at 65° C. for 12 hours, poured into H₂O/CH₂Cl₂. The organic layer was separated, dried (over MgSO₄), filtered and the solvent was evaporated to dryness. The residue was crystallized from CH₃CN. The precipitate was filtered off and dried, yield: 0.19 g of f-7 (46%, melting point: 199° C.).

Preparation of Intermediate f-8

LiAlH₄ (0.0012 mol) was added at 5° C. to a mixture of f-7 (0.0002 mol) in THF (15 ml) under N₂ flow. The mixture was stirred at 5° C. for 2 hours, then stirred at room temperature for 4 hours and poured into a minimum of H₂O. CH₂Cl₂ and CH₃OH (few quantity) were added. The organic layer was separated, dried (over MgSO₄), filtered and the solvent was evaporated to dryness. The residue was crystallized from 2-propanone/CH₃CN/Diisopropylether. The precipitate was filtered off and dried, yield: 0.062 g of f-8 (75%, melting point: 199° C.).

Preparation of Intermediate f-9

A mixture of f-8 (0.0036 mol) and MnO₂ (3 g) in CH₂Cl₂ (100 ml) and CH₃OH (2 ml) was stirred at room temperature for 12 hours, and then filtered over celite. The filtrate was evaporated. The residue was purified by column chromatography over silica gel (eluent: CH₂Cl₂/CH₃OH/NH₄OH 96/4/0.5; 15-40 μm). The pure fractions were collected and the solvent was evaporated, yield: 1.1 g of f-9 (74%).

Preparation of Final Compound 58

A mixture of f-9 (0.0003 mol), f-10 (0.0004 mol) and BH₃CN— on solid support (0.0005 mol) in CH₃OH (20 ml) and CH₃CO₂H (0.15 ml) was stirred at room temperature for 12 hours, and then filtered. The filtrate was evaporated to dryness. The residue was taken up in CH₂Cl₂. The organic layer was washed with K₂CO₃ 10%, dried (over MgSO₄), filtered and the solvent was evaporated to dryness. The residue (0.26 g) was purified by column chromatography over silica gel (eluent: CH₂Cl₂/CH₃OH/NH₄OH 91/9/0.5; 10 μm). The pure fractions were collected and the solvent was evaporated. The residue (0.16 g, 78%) was crystallized from CH₃CN/Diisopropylether. The precipitate was filtered off and dried, yield: 0.127 g of compound 59 (62%, melting point: 158° C.).

Example 7

Scheme G

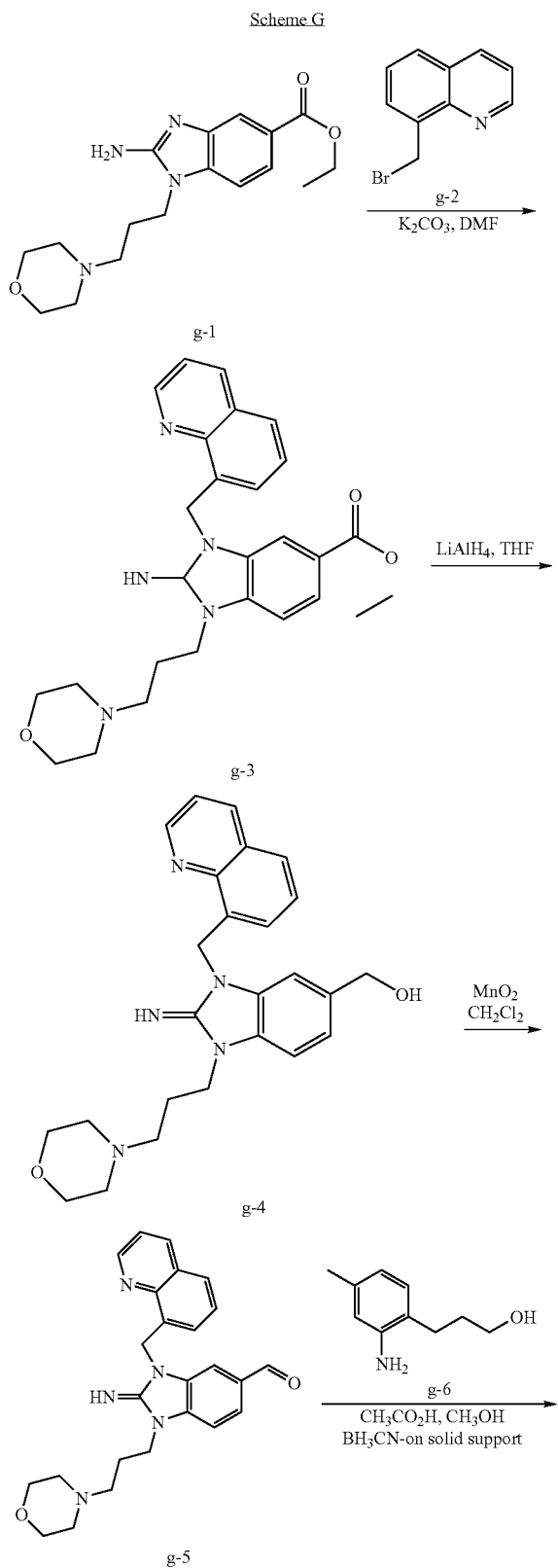

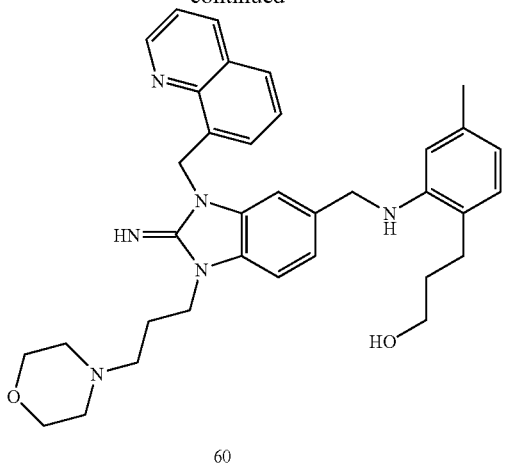

Preparation of Intermediate g-3

A mixture of g-1 (0.003 mol), g-2 (0.0033 mol) and $K_2CO_3$ (0.006 mol) in DMF (50 ml) was stirred at 60° C. for 6 hours, poured into ice water, saturated with $K_2CO_3$ and extracted with $CH_2Cl_2$. The organic layer was separated, dried (over $MgSO_4$), filtered and the solvent was evaporated to dryness. The residue (2.4 g) was purified by column chromatography over silica gel (eluent: $CH_2Cl_2/CH_3OH/NH_4OH$ 93/7/0.5; 20-45 μm). The pure fractions were collected and the solvent was evaporated, yield: 0.63 g of g-3 (44%).

Preparation of Intermediate g-4

A suspension of $LiAlH_4$ (0.0079 mol) in THF (20 ml) was added at 5° C. to a solution of g-3 (0.0013 mol) in THF (20 ml) under $N_2$ flow. The mixture was stirred at 5° C. for 2 hours, then stirred at room temperature for 2 hours and cooled to 5° C. Ice was added. $CH_2Cl_2/CH_3OH$ was added. The organic layer was separated, dried (over $MgSO_4$), filtered and the solvent was evaporated, yielding 0.176 g of g-4 (31%, melting point: 186° C.).

Preparation of Intermediate g-5

A mixture of g-4 (0.0002 mol) and $MnO_2$ (0.3 g) in $CH_2Cl_2$ (10 ml) was stirred at room temperature for 1 hour and 30 minutes, and then filtered over celite. Celite was washed with $CH_2Cl_2$. The filtrate was evaporated to dryness, yielding 0.126 g of g-5.

Preparation of Final Compound 60

A mixture of g-5 (0.0003 mol), g-6 (0.0003 mol), $BH_3CN$— on solid support (0.0004 mol) and $CH_3CO_2H$ (5 drops) in $CH_3OH$ (7 ml) was stirred at room temperature for 24 hours, and then filtered. The filtrate was evaporated to dryness. The residue was taken up in $CH_2Cl_2/CH_3OH/K_2CO_3$ 10%. The mixture was saturated with $K_2CO_3$ (powder) and extracted with $CH_2Cl_2$. The organic layer was separated, dried (over $MgSO_4$), filtered and the solvent was evaporated to dryness. The residue (0.17 g) was purified by column chromatography over silica gel (eluent: $CH_2Cl_2/CH_3OH/NH_4OH$ 89/10/1). The pure fractions were collected and the solvent was evaporated. The residue was taken up in 2-propanone. The precipitate was filtered off and dried, yielding 0.047 g of compound 60 (28%, melting point: 90° C.).

TABLE 1
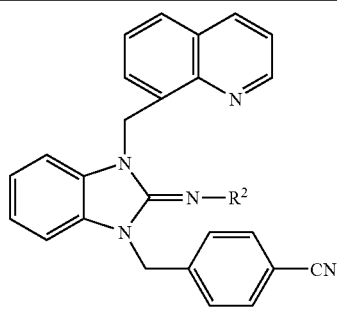
| Comp. No. | R² | pIC50 | MS MH+ | Mp (° C.)/salt | Preparation method |
|---|---|---|---|---|---|
| 1 | 4-(O-(CH₂)₂-OH)-C₆H₄-(CH₂)₂- | 8.2 | 554 | | A |
| 2 | 4-CN-C₆H₄-CH₂- | 8 | 505 | | B |
| 3 | 4-OCH₃-C₆H₄-(CH₂)₂- | 8 | 525 | 168/HCl | A |
| 4 | 4-OH-C₆H₄-(CH₂)₂- | 7.9 | 510 | 160 | A |
| 5 | 4-C(O)OCH₃-C₆H₄-CH₂- | 7.8 | 538 | | B |
| 6 | 4-Br-C₆H₄-(CH₂)₂- | 7.5 | 572 | 178/HCl | A |
| 7 | 4-OH-C₆H₄-(CH₂)₄- | 7.5 | 524 | 82 | C |
| 8 | 3-F-C₆H₄-(CH₂)₂- | 7.3 | 512 | 102 | A |
| 9 | 4-OCH₃-C₆H₄-(CH₂)₃- | 7.3 | 538 | 80 | C |

TABLE 1-continued

| Comp. No. | R² | pIC50 | MS MH+ | Mp (° C.)/salt | Preparation method |
|---|---|---|---|---|---|
| 10 | 3-CN-benzyl | 7.2 | 505 | | B |
| 11 | (CH₂)₂-(4-F-phenyl) | 7.1 | 512 | 102/HCl | A |
| 12 | CH₂-(quinolin-8-yl) | 7.1 | 532 | 168 | B |
| 13 | (CH₂)₃-morpholino | 6.9 | 517 | 80 | A |
| 14 | (CH₂)₂-(2-OCH₃-phenyl) | 6.8 | 524 | HCl | B |
| 15 | (CH₂)₃-(2-oxopyrrolidin-1-yl) | 6.7 | 515 | HCl | A |
| 16 | CH₂-(3,5-diCH₃-phenyl) | 6.6 | 508 | 142 | B |
| 17 | (CH₂)₂-(4-Br-phenyl) | 6.5 | 573 | | B |

TABLE 1-continued

| Comp. No. | R² | pIC50 | MS MH+ | Mp (° C.)/salt | Preparation method |
|---|---|---|---|---|---|
| 18 | -(CH₂)₂-CH(phenyl)₂ | 6.5 | 584 | 184 | A |
| 19 | 3-Cl-benzoyl | 6.5 | 528 | 160 | B |
| 20 | 3-CH₃-benzoyl | 6.4 | 508 | 158 | B |
| 21 | 4-Cl-benzoyl | 6.4 | 528 | 154 | B |
| 22 | 3-NO₂-benzoyl | 6.2 | 539 | 222 | B |
| 23 | 2,4-diCl-benzoyl | 6.2 | 562 | 114 | B |
| 24 | 3,5-di(CF₃)-benzoyl | 6.1 | 630 | 190 | B |

TABLE 1-continued
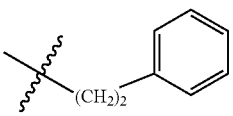
| Comp. No. | R² | pIC50 | MS MH+ | Mp (° C.)/salt | Preparation method |
|---|---|---|---|---|---|
| 25 | 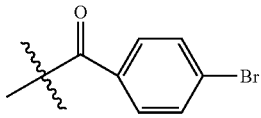 | 5.7 | 494 | | A |
| 26 | 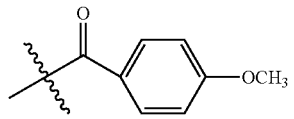 | 5 | 572 | 125 | B |
| 27 | 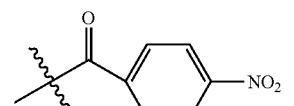 | 4.7 | 524 | 150 | B |
| 28 | 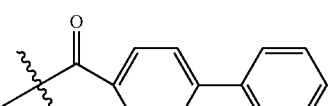 | 4.5 | 539 | 196 | B |
| 29 | 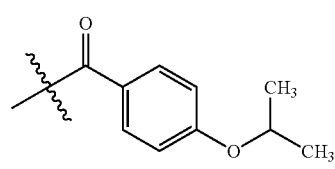 | 4.4 | 570 | 100 | B |
| 30 | 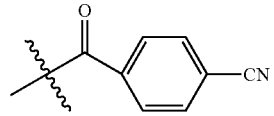 | 4.3 | 552 | 118 | B |
| 31 | 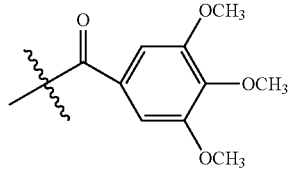 | <4 | 519 | 182 | B |
| 32 |  | <4 | 584 | 108 | B |

TABLE 1-continued
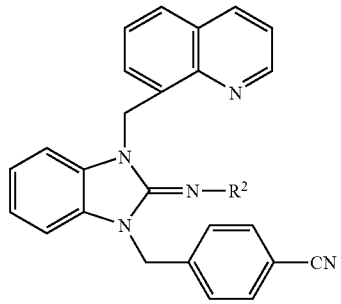
| Comp. No. | R² | pIC50 | MS MH+ | Mp (° C.)/salt | Preparation method |
|---|---|---|---|---|---|
| 33 | ![structure] | 4 | 586 | 66 | B |
TABLE 2
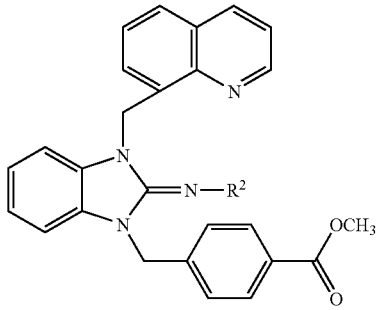
| Comp. No. | R² | pIC50 | MS MH+ | Mp (° C.)/salt | Preparation method |
|---|---|---|---|---|---|
| 34 | —(CH₂)₂—C₆H₄—OCH₃ | | | | |
| 35 | —(CH₂)₂—C₆H₄—Br | 8.1 | 605 | 128/HCl | C |
| 36 | —(CH₂)₂—C₆H₄—F | 7.1 | 545 | 89 | A |
| 37 | —(CH₂)₃—N(morpholine) | 6.9 | 550 | 96/HCl | A |

TABLE 2-continued

[Structure: benzimidazole with N-CH2-quinolin-8-yl, =N-R2, and N-CH2-C6H4-C(=O)OCH3 substituents]

| Comp. No. | R2 | pIC50 | MS MH+ | Mp (° C.)/salt | Preparation method |
|---|---|---|---|---|---|
| 38 | [-CH(CH2)CH(C6H5)2 / diphenylpropyl group] | 6.8 | 617 | 146 | A |
| 39 | [-C(=O)-3,5-bis(CF3)phenyl] | 5.8 | 663 | 204 | B |
| 40 | [-C(=O)-4-Br-phenyl] | <4 | 605 | 131 | B |

TABLE 3

[Structure: benzimidazole with N-CH2-quinolin-8-yl, =N-R2, and N-R3]

| Comp. No. | R2 | R3 | pIC50 | MS MH+ | Mp (° C.) | Prep. method |
|---|---|---|---|---|---|---|
| 41 | -(CH2)2-C6H4-OCH3 | -CH2-C6H4-OCH3 | 7.2 | 529 | | A |
| 42 | -(CH2)2-C6H4-OCH3 | -CH2-C6H4-CH3 | 7.1 | 513 | | A |

TABLE 3-continued
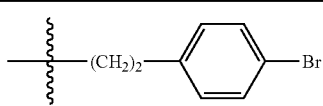
| Comp. No. | R² | R³ | pIC50 | MS MH+ | Mp (° C.) | Prep. method |
|---|---|---|---|---|---|---|
| 43 | —(CH₂)₂—C₆H₄—Br | —CH₂—C₆H₄—C(O)OCH₃ | 7.1 | 605 | 80 | C |
| 44 | —(CH₂)₂—C₆H₄—Br | —CH₂—C₆H₄—OCH₃ | 7.1 | 577 | 87 | C |
| 45 | —(CH₂)₂—C₆H₄—OCH₃ | —CH₂—C₆H₄—Br | 7 | 577 | | A |
| 46 | —(CH₂)₂—C₆H₄—OCH₃ | —CH₂—C₆H₄—Cl | 7 | 533 | 250 | A |
| 47 | —(CH₂)₂—C₆H₄—OCH₃ | —CH₂—C₆H₄—F | 6.8 | 517 | | A |
| 48 | —(CH₂)₂—C₆H₄—OCH₃ | —(CH₂)₂—C₆H₄—O—CH₂—CH₃ | 6.7 | 557 | 102/HCl | C |
| 49 | —(CH₂)₂—C₆H₄—OCH₃ | —CH₂—C₆H₄—Cl | 6.6 | 533 | 172/HCl | A |
| 50 | —(CH₂)₂—C₆H₄—Br | —CH₂—C(O)—C₆H₄—OCH₃ | 6.5 | 605 | 152 | C |
| 51 | —(CH₂)₂—C₆H₄—Br | —(CH₂)₂—C₆H₄—O—C₂H₅ | 6.3 | 605 | 96/HCl | C |

TABLE 3-continued

[Structure: benzimidazole with quinolin-8-ylmethyl on N, =N-R² and N-R³]

| Comp. No. | R² | R³ | pIC50 | MS MH+ | Mp (° C.) | Prep. method |
|---|---|---|---|---|---|---|
| 52 | —(CH₂)₂—C₆H₄—Br (4-Br) | —C(=O)—C₆H₄—Br (4-Br) | 6.2 | 653 | 120 | C |
| 53 | —(CH₂)₂—C₆H₄—Br (4-Br) | —C(=O)—C₆H₄—CN (4-CN) | 5.6 | 600 | | C |
| 54 | —(CH₂)₂—C₆H₄—Br (4-Br) | —CH₂—C₆H₄—OH (3-OH) | | 577 | | C |

TABLE 4

[Structure: benzimidazole with R¹ on N, =N-R², and N-CH₂-C₆H₄-CN (4-CN)]

| Comp. No. | R¹ | R² | pIC50 | MS MH+ | Mp (° C.)/ salt | Prep. method |
|---|---|---|---|---|---|---|
| 55 | 3-hydroxy-6-methylpyridin-2-ylmethyl | 4-(2-aminoethyl)piperidin-1-yl (piperidine-CH₂CH₂NH₂) | 7.2 | 496 | | D |
| 56 | quinolin-2-ylmethyl | —(CH₂)₃—morpholine | 6.7 | 517 | 150/oxalate | B |
| 57 | 3-hydroxy-6-methylpyridin-2-ylmethyl | —(CH₂)₂—C₆H₄—Br (4-Br) | 6.6 | 552 | 204 | A |

TABLE 5

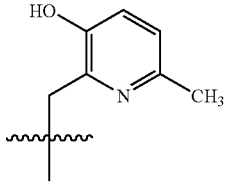

| Comp. No. | R¹ | R³ | pIC50 | MS MH+ | Mp (° C.) | Prep. method |
|---|---|---|---|---|---|---|
| 58 | 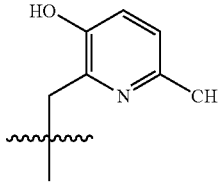 | CH₃ | 8.5 | 446 | 195 | E |
| 59 | 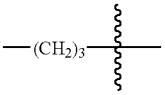 | 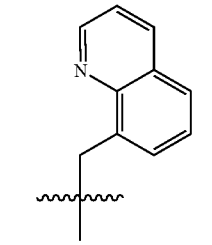 | 4 | 559 | 158 | F |
| 60 | 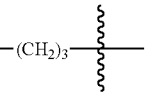 | 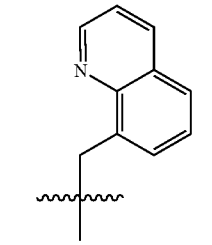 | 6.4 | 579 | 90 | G |

Example 8

In vitro screening of compounds of formula (I) for activity against RSV. The percent protection against cytopathology caused by viruses (antiviral activity or $EC_{50}$) achieved by tested compounds and their cytotoxicity ($CC_{50}$) are both calculated from dose-response curves. The selectivity of the antiviral effect is represented by the selectivity index (SI), calculated by dividing the $CC_{50}$ (cytotoxic dose for 50% of the cells) by the $EC_{50}$ (antiviral activity for 50% of the cells). The tables in the above experimental part list the category to which each of the prepared compounds belong: Compounds belonging to activity category "A" have a $pEC_{50}$ (-log of $EC_{50}$ when expressed in molar units) equal to or more than 7. Compounds belonging to activity category "B" have a pEC50 value between 6 and 7. Compounds belonging to activity category "C" have a pEC50 value equal to or below 6.

Automated tetrazolium-based colorimetric assays were used for determination of $EC_{50}$ and $CC_{50}$ of test compounds. Flat-bottom, 96-well plastic microtiter trays were filled with 180 µl of Eagle's Basal Medium, supplemented with 5% FCS (0% for FLU) and 20 mM Hepes buffer. Subsequently, stock solutions (7.8×final test concentration) of compounds were added in 45 µl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 $TCID_{50}$ of Respiratory Syncytial Virus was added to two of the three rows in a volume of 50 µl. The same volume of medium was added to the third row to measure the cytotoxicity of the compounds at the same concentrations as those used to measure the antiviral activity. After two hours of incubation, a suspension ($4 \times 10^5$ cells/ml) of HeLa cells was added to all wells in a volume of 50 µl. The cultures were incubated at 37° C. in a 5% $CO_2$ atmosphere. Seven days after infection the cytotoxicity and the antiviral activity was examined spectrophotometrically. To each well of the microtiter tray, 25 µl of a solution of MTT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 µl 2-propanol. Complete dissolution of the formazan crystals was obtained after the trays have been placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, so as to eliminate the effects of non-specific absorption.

The percent protection against cytopathology caused by viruses (antiviral activity or $EC_{50}$) achieved by tested compounds and their cytotoxicity ($CC_{50}$) were both calculated from dose-response curves. The selectivity of the antiviral effect is represented by the selectivity index (SI), calculated by dividing the $CC_{50}$ (cytotoxic dose for 50% of the cells) by the $EC_{50}$ (antiviral activity for 50% of the cells).

The invention claimed is:

1. A compound of formula

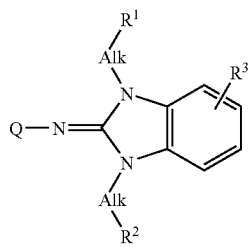
(I)

or an addition salt thereof; or a stereochemically isomeric form thereof; wherein each Alk independently is $C_{1-6}$alkanediyl;

Q is hydrogen; $C_{1-6}$alkyl substituted with one or two $Ar^2$ radicals; $C_{1-6}$alkyl substituted with quinolinyl, oxazolidinyl, thiazolidinyl, morpholinyl, thiomorpholinyl, or with pyrrolidinonyl; —CO—$Ar^2$; or Q is a radical of formula (a)

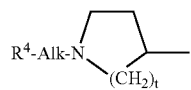
(a)

wherein t is 1, 2 or 3;
$R^4$ is amino, mono-or di($C_{1-6}$alkyl)amino;
$R^1$ is a monocyclic or bicyclic heterocycle selected from piperidinyl, piperazinyl, morpholinyl, thiomorpholinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]pyridinyl and 2,3-dihydro-1,4-dioxino[2,3-b]pyridyl;
wherein each of said monocyclic or bicyclic heterocycles may optionally be substituted with 1, 2, or 3 substituents each independently selected from the group consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, hydroxy$C_{1-6}$alkyl, mono-or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyloxycarbonyl and —C(=O)—$NR^{5a}R^{5b}$;
$R^2$ is hydrogen, $Ar^2$, —CO—$Ar^2$ or a monocyclic or bicyclic heterocycle selected from piperidinyl, piperazinyl, morpholinyl, thiomorpholinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]pyridinyl and 2,3-dihydro-1,4-dioxino[2,3-b]pyridyl;
wherein each of said monocyclic or bicyclic heterocycles may optionally be substituted with 1, 2, or 3 substituents each independently selected from the group consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, hydroxy$C_{1-6}$alkyl, mono-or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyloxycarbonyl and —C(=O)—$NR^{5a}R^{5b}$;
where Q is other than hydrogen, $R^3$ is hydrogen; or where Q is hydrogen, $R^3$ is a radical of formula (b):

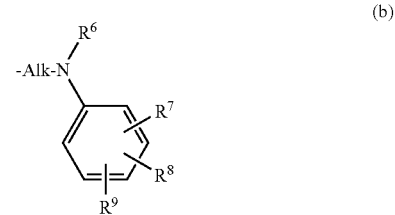
(b)

wherein
$R^6$ is selected from hydrogen, $C_{1-6}$alkyl, $Ar^2C_{1-6}$alkyl, hydroxy$C_{1-6}$alkyl, ($C_{1-6}$alkyloxy)-$C_{1-6}$alkyl, amino-$C_{1-6}$alkyl, mono- and di($C_{1-6}$alkyl)amino-$C_{1-6}$alkyl, carboxyl$C_{1-6}$alkyl, $C_{1-6}$alkyloxycarbonyl$C_{1-6}$alkyl, aminocarbonyl$C_{1-6}$alkyl, mono- and di($C_{1-6}$alkyl)aminocarbonyl$C_{1-6}$alkyl;
$R^7$, $R^8$, and $R^9$ each independently are selected from halo, cyano, $C_{1-6}$alkyl $Ar^1$ $C_{1-6}$alkyl, cyano$C_{1-6}$alkyl, $C_{2-6}$alkenyl, cyano$C_{2-6}$alkenyl, $C_{2-6}$alkynyl, cyano$C_{2-6}$alkynyl, $Ar^1$, $R^{10a}$—O—, $R^{10a}$—S—, $N(R^{5a}R^{5b})$, polyhalo$C_{1-6}$alkyl, $R^{10a}$—O—C(=O)—, $N(R^{5a}R^{5b})$—C(=O)—, $R^{10a}$—O—$C_{1-6}$alkyl, $N(R^{5a}R^{5b})$—$C_{1-6}$alkyl, $R^{10a}$—O—C(=O)—$C_{1-6}$alkyl, $N(R^{5a}R^{5b})$—C(=O)—$C_{1-6}$alkyl, $R^{10a}$—C(=O)—$NR^{5b}$—, $R^{10b}$—C(=O)—O—, $R^{10b}$—C(=O)—O—$C_{1-6}$alkyl; and $R^8$ and/or $R^9$ may also be hydrogen;
each $R^{5a}$ and $R^{5b}$ independently from each other are hydrogen or $C_{1-6}$alkyl;
$R^{10a}$ is hydrogen, $C_{1-6}$alkyl or $Ar^1C_{1-6}$alkyl;
$R^{10b}$ is $C_{1-6}$alkyl or $Ar^1C_{1-6}$alkyl;
$Ar^1$ is phenyl or phenyl substituted with 1, 2, 3 or 4 substituents independently selected from halo, hydroxy, hydroxy$C_{1-6}$alkyl, polyhalo$C_{1-6}$alkyl and $C_{1-6}$alkyloxy;
$Ar^2$ is phenyl or phenyl substituted with 1, 2, 3 or 4 substituents independently selected from halo, hydroxy, cyano, nitro, hydroxy$C_{1-6}$alkyl, polyhalo$C_{1-6}$alkyl, $C_{1-6}$alkyloxy, hydroxy$C_{1-6}$alkyloxy, $C_{1-6}$alkyloxycarbonyl, $Ar^1$ and $Ar^1O$.

2. A compound as claimed in claim 1 wherein Q is hydrogen; $C_{1-6}$alkyl substituted with one or two $Ar^2$ radicals; $C_{1-6}$alkyl substituted with quinolinyl, morpholinyl or with pyrrolidinonyl; —CO—$Ar^2$; or Q is a radical of formula (a)

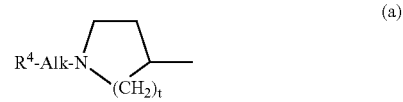
(a)

wherein t is 2; and $R^4$ is amino, mono-or di($C_{1-6}$alkyl)amino.

3. A compound according to claim 1 wherein Q is hydrogen.

4. A compound according to claim 1 wherein Q is $C_{1-6}$alkyl substituted with one or two $Ar^2$ radicals; $C_{1-6}$alkyl substituted with quinolinyl, morpholinyl or with pyrrolidinonyl; or Q is —CO—$Ar^2$; or Q is a radical of formula (a) wherein t is 2; and $R^4$ is amino, mono-or di($C_{1-6}$alkyl)amino.

5. A compound according to claim 1 wherein $R^1$ is morpholinyl or quinolinyl, and $R^2$ is $Ar^2$, —CO—$Ar^2$, morpholinyl or quinolinyl.

6. A compound according to claim 1 wherein $R^2$ is hydrogen.

7. A compound according to claim 1 wherein $R^3$ is a radical of formula (b) wherein
- $R^6$ is selected from hydrogen, hydroxy$C_{1-6}$alkyl, amino-$C_{1-6}$alkyl and aminocarbonyl-$C_{1-6}$alkyl;
- $R^7$, $R^8$, and $R^9$ independently from one another are selected from halo, $C_{1-6}$alkyl, cyano$C_{1-6}$alkyl, $R^{10a}$—O—, —N($R^{5a}R^{5b}$), $R^{10a}$—O—$C_{1-6}$alkyl, N($R^{5a}R^{5b}$)—$C_{1-6}$alkyl,
- $R^{10a}$—O—C(=O)—$C_{1-6}$alkyl, $R^{10b}$—C(=)—O—$C_{1-6}$alkyl; and $R^8$ and/or $R^9$ may also be hydrogen;
- $R^{5a}$ and $R^{5b}$ are hydrogen;
- $R^{10a}$ is hydrogen or $C_{1-6}$alkyl; and
- $R^{10b}$ is $C_{1-6}$alkyl.

8. A compound according to claim 1 wherein $R^3$ is hydrogen or a radical of formula (b) wherein
- $R^6$ is hydrogen;
- $R^7$, $R^8$, and $R^9$ independently from one another are selected from $C_{1-6}$alkyl,
- $R^{10a}$—O—$C_{1-6}$alkyl, and $R^8$ and/or $R^9$ may also be hydrogen;
- $R^{5a}$ and $R^{5b}$ are hydrogen; and
- $R^{10a}$ is hydrogen or $C_{1-6}$alkyl.

9. A compound according to claim 1 wherein $R^3$ is hydrogen.

10. A pharmaceutical composition comprising a pharmaceutically acceptable carrier, and as active ingredient a therapeutically effective amount of a compound of claim 1.

11. A process for preparing a chemical compound according to claim 1 of the formula

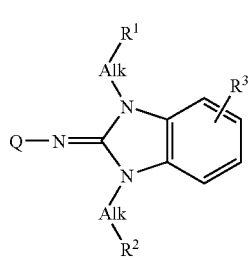

(I)

said process comprising:

(a) N-alkylating a benzimidazole (II) with an alkylating agent (III) as outlined in the following reaction scheme:

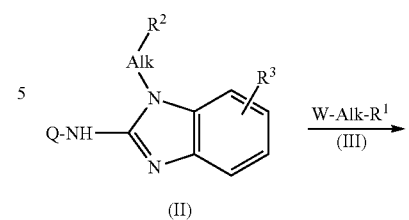

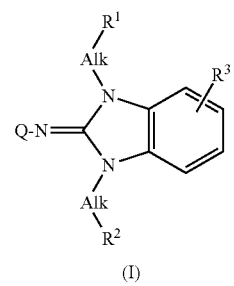

wherein in this and the following reaction schemes Q, Alk, $R^1$, $R^2$, $R^3$, $R^4$ have the meanings defined in claim 1 and W represents a leaving group; or (b) N-alkylating or N-acylating (where Q is $Ar^2$—CO—) a benzimidazole (IV) with an alkylating or acylating agent (V) as outlined in the following reaction scheme:

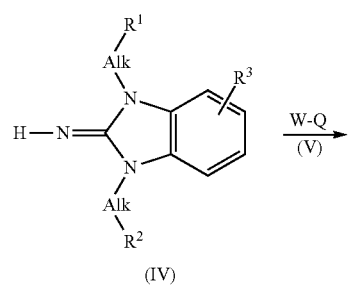

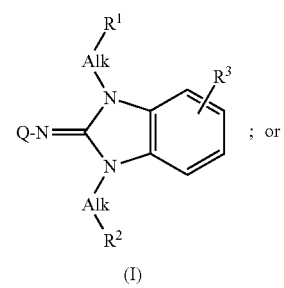

(c) preparing compounds of formula (I) wherein $R^3$ is a radical (b) wherein the group Alk is methylene, which compounds can be represented by formula (I-a) by reducing intermediates of formula (VI) wherein $R^{11}$ is $C_{1-6}$alkyl, by a reduction reaction, to intermediates (VII) having a hydroxymethylene group and oxidizing the latter group to an aldehyde group (intermediates VIII) with a mild oxidant, which can further be derivatized with amines to the compounds of formula (I-a):

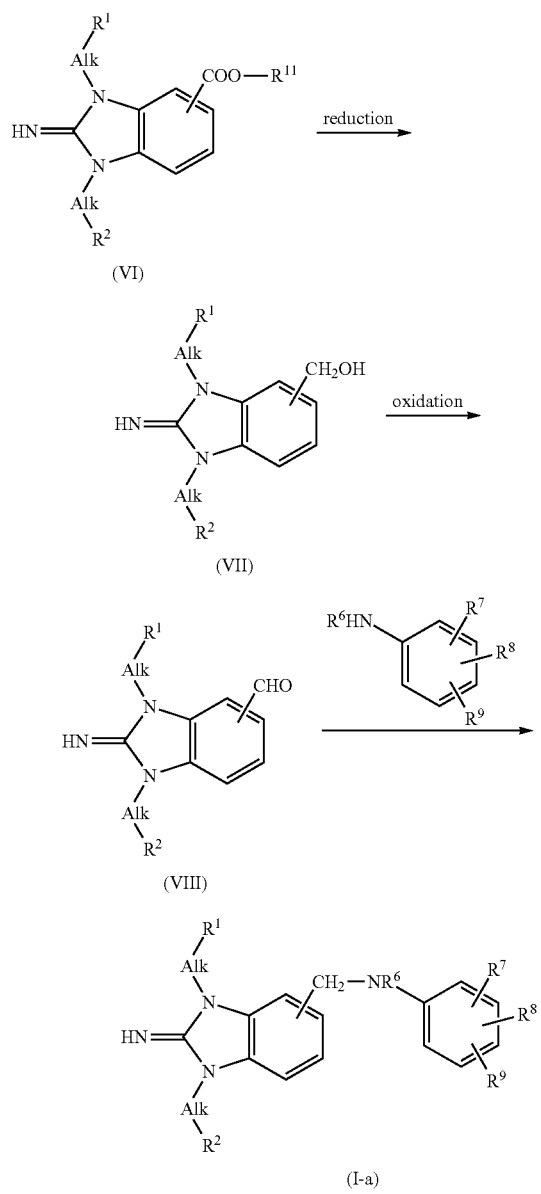

(VI) reduction →

(VII) oxidation →

(VIII)

(I-a) ; or (d) preparing compounds of formula (I) wherein Q is a radical (a), which compounds can be represented by formula (I-b) N-alkylating intermediates of formula (IX) with a reagent R⁴—Alk—W:

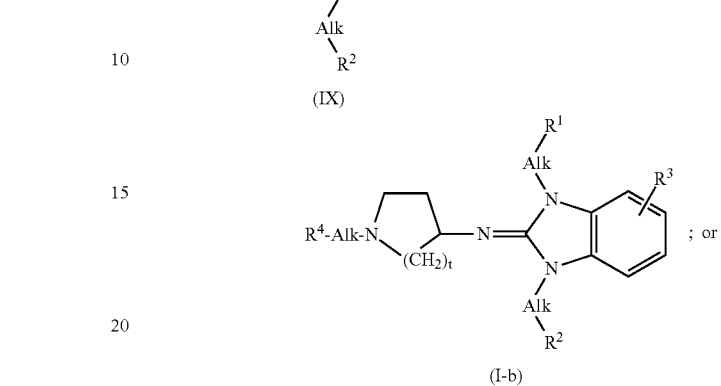

(IX) R⁴-Alk-W →

(I-b) ; or (e) converting compounds of formula (I) into each other following art-known functional group transformation reactions.

12. A method for treating a respiratory syncytial viral infection comprising administering to a subject in need thereof an anti-virally effective amount of a compound of claim 1.

13. A pharmaceutical composition comprising a compound of claim 1 made by mixing a compound of claim 1 and a pharmaceutically acceptable carrier.

14. A process for making a pharmaceutical composition comprising mixing a compound of claim 1 and a pharmaceutically acceptable carrier.

15. The pharmaceutical composition of claim 10, further comprising an antiviral agent.

16. The pharmaceutical composition of claim 15, further comprising an antiviral agent selected from the group consisting of interferon-beta and tumor necrosis factor-alpha.

17. A method of treating a warm-blooded animal infected by a respiratory syncytial virus comprising administering to the warm-blooded animal an anti-virally effective amount of a compound of claim 1.

18. A method of treating a warm-blooded animal infected by a respiratory syncytial virus comprising administering to the warm-blooded animal an anti-virally effective amount of a compound of claim 1 and an antiviral agent.

19. The method of claim 18, wherein the antiviral agent is selected from the group consisting of interferon-beta and tumor necrosis factor-alpha.

* * * * *